US009545321B2

(12) United States Patent
Hibri et al.

(10) Patent No.: US 9,545,321 B2
(45) Date of Patent: Jan. 17, 2017

(54) PROSTHETIC SPINAL DISK NUCLEUS

(71) Applicant: Spinal Stabilization Technologies, LLC, Austin, TX (US)

(72) Inventors: Nadi Salah Hibri, San Antonio, TX (US); James Douglas Lutz, San Antonio, TX (US)

(73) Assignee: SPINAL STABILIZATION TECHNOLOGIES LLC, San Antonio, TX (US)

( * ) Notice: Subject to any disclaimer, the term of this patent is extended or adjusted under 35 U.S.C. 154(b) by 0 days.

(21) Appl. No.: 14/536,497

(22) Filed: Nov. 7, 2014

(65) Prior Publication Data

US 2015/0057752 A1    Feb. 26, 2015

Related U.S. Application Data

(63) Continuation of application No. 13/831,257, filed on Mar. 14, 2013.

(51) Int. Cl.
*A61F 2/44* (2006.01)
*A61B 17/88* (2006.01)
(Continued)

(52) U.S. Cl.
CPC .............. *A61F 2/4611* (2013.01); *A61F 2/44* (2013.01); *A61B 17/1671* (2013.01); *A61F 2002/3024* (2013.01); *A61F 2002/30092* (2013.01); *A61F 2002/30235* (2013.01); *A61F 2002/30448* (2013.01); *A61F 2002/30579* (2013.01); *A61F 2002/30584* (2013.01); *A61F 2002/30586* (2013.01); *A61F 2002/444* (2013.01); *A61F 2002/4435* (2013.01);
(Continued)

(58) Field of Classification Search
CPC ...... A61B 17/7097; A61F 2/441; A61F 2/442; A61F 2002/444; A61F 2002/30583; A61F 2002/30584; A61F 2002/30586; A61F 2002/30581
See application file for complete search history.

(56) References Cited

U.S. PATENT DOCUMENTS 3,875,595 A    4/1975  Froning
5,192,326 A    3/1993  Bao et al.
(Continued)

FOREIGN PATENT DOCUMENTS

KR    20120040309 A    4/2012
WO    WO2007/087404 A2    8/2007

OTHER PUBLICATIONS

Birkenmaier et al., Minimally Invasive Endoscopic Spinal Surgery, www.spineuniverse.com/displayarticle.pho/article_2016.html [Jun. 15, 2009].
(Continued)

*Primary Examiner* — Jacqueline Johanas
(74) *Attorney, Agent, or Firm* — Norton Rose Fulbright US LLP

(57) ABSTRACT

This specification describes technologies relating to an intervertebral disc prosthesis used to strengthen and stabilize the spine. Implementations of the technology described herein comprise a surgical device that is implanted through a small surgical incision into a portion of a human intervertebral disc, various support tools used to insert such a surgical device, and a method by which the device is used to strengthen and stabilize the spine.

15 Claims, 17 Drawing Sheets

(51) Int. Cl.
*A61F 2/46* (2006.01)
*A61F 2/30* (2006.01)
*A61B 17/16* (2006.01)

(52) U.S. Cl.
CPC ............... *A61F 2002/4627* (2013.01); *A61F 2002/4693* (2013.01); *A61F 2002/4694* (2013.01); *A61F 2250/0003* (2013.01); *A61F 2250/0069* (2013.01)

(56) References Cited

U.S. PATENT DOCUMENTS

| | | |
|---|---|---|
| 5,439,464 A | 8/1995 | Shapiro |
| 5,571,189 A | 11/1996 | Kuslich |
| 5,645,597 A | 7/1997 | Krapiva |
| 5,674,295 A | 10/1997 | Ray et al. |
| 5,702,449 A | 12/1997 | McKay |
| 5,865,845 A | 2/1999 | Thalgott |
| 5,888,220 A | 3/1999 | Felt et al. |
| 5,890,268 A | 4/1999 | Mullen et al. |
| 5,981,826 A | 11/1999 | Ku et al. |
| 5,990,378 A | 11/1999 | Ellis |
| 6,127,597 A | 10/2000 | Beyer et al. |
| 6,146,419 A | 11/2000 | Eaton ........................ 623/11.11 |
| 6,183,518 B1 | 2/2001 | Ross et al. ................. 623/17.16 |
| 6,248,131 B1 | 6/2001 | Felt et al. ................... 623/17.12 |
| 6,264,695 B1 | 7/2001 | Stoy |
| 6,332,894 B1 | 12/2001 | Stalcup et al. |
| 6,375,682 B1 | 4/2002 | Fleischmann et al. |
| 6,390,992 B1 | 5/2002 | Morris et al. |
| 6,395,032 B1 | 5/2002 | Gauchet |
| 6,419,704 B1 | 7/2002 | Ferree |
| 6,436,143 B1 | 8/2002 | Ross et al. |
| 6,443,988 B2 | 9/2002 | Felt et al. ................... 623/17.12 |
| 6,482,234 B1 | 11/2002 | Weber et al. |
| 6,527,804 B1 | 3/2003 | Gauchet et al. |
| 6,533,818 B1 | 3/2003 | Weber et al. ............... 623/17.16 |
| 6,582,466 B1 | 6/2003 | Gauchet ..................... 623/17.11 |
| 6,596,008 B1 | 7/2003 | Kambin |
| 6,645,248 B2 | 11/2003 | Casutt ........................ 623/17.12 |
| 6,712,853 B2 | 3/2004 | Kuslich |
| 6,733,532 B1 | 5/2004 | Gauchet et al. |
| 6,733,533 B1 | 5/2004 | Lozier ........................ 623/17.12 |
| 6,852,095 B1 | 2/2005 | Ray |
| 6,866,681 B2 | 3/2005 | Laboureau et al. |
| 6,893,465 B2 | 5/2005 | Huang ........................ 623/17.12 |
| 6,893,466 B2 | 5/2005 | Trieu |
| 6,932,843 B2 | 8/2005 | Smith et al. ................ 623/17.11 |
| 6,936,070 B1 | 8/2005 | Muhanna .................... 623/17.12 |
| 6,958,077 B2 | 10/2005 | Suddaby |
| 6,969,404 B2 | 11/2005 | Ferree |
| 6,969,405 B2 | 11/2005 | Suddaby ..................... 623/17.12 |
| 7,001,431 B2 | 2/2006 | Bao et al. |
| 7,004,971 B2 | 2/2006 | Serhan et al. |
| 7,008,427 B2 | 3/2006 | Sevrain |
| 7,056,345 B2 | 6/2006 | Kuslich |
| 7,077,865 B2 | 7/2006 | Bao et al. |
| 7,133,001 B2 | 11/2006 | Mrstik et al. |
| 7,156,861 B2 | 1/2007 | Scribner et al. ............... 606/192 |
| 7,156,877 B2 | 1/2007 | Lotz et al. .................. 623/17.16 |
| 7,182,783 B2 | 2/2007 | Trieu |
| 7,201,751 B2 | 4/2007 | Zucherman et al. |
| 7,201,776 B2 | 4/2007 | Ferree et al. |
| 7,204,851 B2 | 4/2007 | Trieu et al. |
| 7,220,282 B2 | 5/2007 | Kuslich |
| 7,273,497 B2 | 9/2007 | Ferree |
| 7,309,359 B2 | 12/2007 | Trieu et al. |
| 7,556,650 B2 | 7/2009 | Collins et al. .............. 623/17.11 |
| 7,563,284 B2 | 7/2009 | Coppes et al. .............. 623/17.12 |
| 7,632,294 B2 | 12/2009 | Milbodker et al. |
| 7,641,691 B2 | 1/2010 | Lotz et al. .................. 623/17.12 |
| 7,645,301 B2 | 1/2010 | Hudgins et al. ............. 623/17.12 |
| 7,713,301 B2 | 5/2010 | Bao et al. ................... 623/17.12 |
| 7,722,612 B2 | 5/2010 | Sala et al. |
| 7,731,753 B2 | 6/2010 | Reo et al. ................... 623/17.13 |
| 7,766,965 B2 | 8/2010 | Bao et al. ................... 623/17.12 |
| 7,789,913 B2 | 9/2010 | Collins et al. .............. 623/17.12 |
| 7,799,079 B2 | 9/2010 | Hestad et al. ............... 623/17.12 |
| 7,837,733 B2 | 11/2010 | Collins et al. .............. 623/17.12 |
| 7,842,055 B2 | 11/2010 | Pintor et al. |
| 7,896,920 B2 | 3/2011 | Yuksel et al. ............... 623/17.16 |
| 7,931,689 B2 | 4/2011 | Hochschuler et al. ...... 623/17.12 |
| 7,947,079 B2 | 5/2011 | Helm et al. ................. 623/17.12 |
| 7,972,351 B2 | 7/2011 | Trinidad |
| 7,993,351 B2 | 8/2011 | Worley et al. |
| 7,993,404 B2 | 8/2011 | Trieu ......................... 623/17.12 |
| 7,998,210 B2 | 8/2011 | Edie et al. .................. 623/17.11 |
| 8,012,210 B2 | 9/2011 | Lin et al. .................... 623/17.12 |
| 8,012,211 B2 | 9/2011 | Kuslich ...................... 623/17.12 |
| 8,043,381 B2 | 10/2011 | Hestad et al. ............... 623/17.16 |
| 8,066,758 B2 | 11/2011 | Bogert et al. |
| 8,083,800 B2 | 12/2011 | Edie ........................... 623/17.16 |
| 8,092,536 B2 | 1/2012 | Ahrens et al. .............. 623/17.11 |
| 8,100,978 B2 | 1/2012 | Bass .......................... 623/17.16 |
| 8,123,808 B2 | 2/2012 | Dewey et al. .............. 623/17.12 |
| 8,133,250 B2 | 3/2012 | Parsonage et al. |
| 8,142,489 B2 | 3/2012 | Doran et al. |
| 8,236,057 B2 | 8/2012 | Wirtel, III et al. ......... 623/17.12 |
| 8,246,682 B2 | 8/2012 | Slivka et al. ............... 623/17.11 |
| 8,287,595 B2 | 10/2012 | Vresilovic et al. ......... 623/17.12 |
| 8,292,961 B2 | 10/2012 | Osman ....................... 623/17.12 |
| 8,317,864 B2 | 11/2012 | Kim ........................... 623/17.11 |
| 8,337,556 B2 | 12/2012 | Shaolian et al. ............ 623/17.12 |
| 8,337,557 B2 | 12/2012 | Collins et al. .............. 623/17.12 |
| 8,349,013 B2 | 1/2013 | Zucherman et al. ........ 623/17.12 |
| 8,377,131 B2 | 2/2013 | Lin ............................ 623/17.12 |
| 8,377,136 B2 | 2/2013 | Simonton .................. 623/17.16 |
| 8,377,138 B2 | 2/2013 | Reo et al. ................... 623/17.16 |
| 8,382,838 B2 | 2/2013 | Baumgartner et al. ..... 623/17.12 |
| 8,398,511 B2 | 3/2013 | Sandusky .................... 473/604 |
| 8,403,987 B2 | 3/2013 | Reo et al. ................... 623/17.11 |
| 8,444,694 B2 | 5/2013 | Collins et al. .............. 623/17.12 |
| 8,454,612 B2 | 6/2013 | Lambrecht et al. ......... 606/86 R |
| 8,460,383 B2 | 6/2013 | Wirtel, III et al. ......... 623/17.12 |
| 8,480,718 B2 | 7/2013 | Protopsaltis et al. ......... 606/331 |
| 8,540,772 B2 | 9/2013 | Osman ....................... 623/17.12 |
| 8,551,172 B2 | 10/2013 | Park ........................... 623/17.12 |
| 8,562,634 B2 | 10/2013 | Middleton .................... 606/170 |
| 8,603,171 B2 | 12/2013 | McClellan, III et al. . 623/17.16 |
| 8,636,803 B2 | 1/2014 | Hibri et al. ................. 623/17.12 |
| 8,663,328 B2 | 3/2014 | Justis et al. ................. 623/17.12 |
| 8,690,919 B2 | 4/2014 | Lange et al. .................. 606/249 |
| 8,727,920 B2 | 5/2014 | Sandusky .................... 473/603 |
| 8,734,459 B1 | 5/2014 | Alobaid ......................... 606/92 |
| 8,747,475 B2 | 6/2014 | Kuslich ...................... 623/17.16 |
| 8,808,381 B2 | 8/2014 | Kim et al. ................... 623/17.13 |
| 8,888,850 B2 | 11/2014 | Linares ...................... 623/17.12 |
| 8,894,563 B2 | 11/2014 | Connors et al. ................ 600/30 |
| 8,945,223 B2 | 2/2015 | Trieu ......................... 623/17.12 |
| 8,979,931 B2 | 3/2015 | Stad et al. ................... 623/17.12 |
| 2002/0026244 A1 | 2/2002 | Trieu |
| 2002/0147497 A1 | 10/2002 | Belef et al. |
| 2003/0028251 A1 | 2/2003 | Mathews |
| 2003/0199979 A1 | 10/2003 | McGuckin, Jr. |
| 2004/0106999 A1 | 6/2004 | Mathews |
| 2004/0186471 A1 | 9/2004 | Trieu |
| 2004/0230309 A1 | 11/2004 | DiMauro et al. |
| 2005/0015150 A1 | 1/2005 | Lee |
| 2005/0055099 A1 | 3/2005 | Ku |
| 2005/0065609 A1 | 3/2005 | Wardlaw |
| 2005/0090901 A1 | 4/2005 | Studer |
| 2005/0197702 A1 | 9/2005 | Coppes et al. |
| 2005/0251259 A1 | 11/2005 | Suddaby |
| 2005/0278029 A1 | 12/2005 | Trieu |
| 2006/0247780 A1 | 11/2006 | Bert |
| 2006/0293749 A1 | 12/2006 | Hudgins et al. |
| 2007/0060924 A1 | 3/2007 | Choi |
| 2007/0073402 A1 | 3/2007 | Vresilovic |
| 2007/0093906 A1 | 4/2007 | Hudgins |
| 2007/0135921 A1 | 6/2007 | Park |
| 2007/0150061 A1 | 6/2007 | Trieu |
| 2007/0162136 A1 | 7/2007 | O'Neil et al. |
| 2007/0168031 A1 | 7/2007 | Hudgins et al. |
| 2007/0173935 A1 | 7/2007 | O'Neil et al. |

(56) References Cited

U.S. PATENT DOCUMENTS

| | | |
|---|---|---|
| 2007/0173940 A1 | 7/2007 | Hestad et al. |
| 2007/0213732 A1 | 9/2007 | Khanna et al. |
| 2007/0255406 A1 | 11/2007 | Trieu |
| 2007/0270953 A1 | 11/2007 | Trieu |
| 2008/0046082 A1 | 2/2008 | Lee |
| 2008/0058932 A1 | 3/2008 | Trieu et al. |
| 2008/0154367 A1 | 6/2008 | Justis |
| 2008/0154368 A1 | 6/2008 | Justis et al. |
| 2008/0154373 A1 | 6/2008 | Protopsaltis et al. |
| 2008/0195210 A1 | 8/2008 | Milijasevic et al. ........ 623/17.16 |
| 2008/0288074 A1 | 11/2008 | O'Neil et al. |
| 2009/0012618 A1 | 1/2009 | Ahrens et al. |
| 2009/0076609 A1 | 3/2009 | Stewart ........................ 623/17.16 |
| 2009/0076610 A1 | 3/2009 | Afzal ........................... 623/17.16 |
| 2009/0105823 A1 | 4/2009 | Williams et al. ............ 623/17.16 |
| 2009/0112323 A1 | 4/2009 | Hestad et al. |
| 2009/0118833 A1 | 5/2009 | Hudgins et al. ............ 623/17.16 |
| 2009/0299476 A1 | 12/2009 | Diwan et al. ............... 623/17.12 |
| 2010/0030216 A1 | 2/2010 | Arcenio |
| 2010/0256619 A1 | 10/2010 | Teitelbam et al. |
| 2010/0256766 A1 | 10/2010 | Hibri et al. |
| 2010/0292798 A1 | 11/2010 | Maestretti .................... 623/17.12 |
| 2011/0093076 A1 | 4/2011 | Reo et al. ................... 623/17.16 |
| 2011/0190753 A1 | 8/2011 | Forrest |
| 2011/0196499 A1 | 8/2011 | Boucher et al. |
| 2011/0264224 A1 | 10/2011 | Ferree |
| 2012/0089227 A1 | 4/2012 | Jarzem ........................ 623/17.12 |
| 2012/0089229 A1 | 4/2012 | Thramann |
| 2012/0165941 A1 | 6/2012 | Rabiner et al. ............. 623/17.12 |
| 2012/0277862 A1 | 11/2012 | Tornier et al. |
| 2012/0310352 A1 | 12/2012 | DiMauro et al. ........... 623/17.16 |
| 2013/0103155 A1 | 4/2013 | Tornier et al. .............. 623/17.16 |
| 2013/0131806 A1 | 5/2013 | Carpetner ................... 623/17.12 |
| 2013/0297026 A1 | 11/2013 | de Villiers et al. ......... 623/17.12 |
| 2014/0052250 A1 | 2/2014 | Wirtel et al. ................ 623/17.12 |
| 2014/0094914 A1 | 4/2014 | Hibri et al. ................. 623/17.12 |
| 2014/0277467 A1 | 9/2014 | Hibri et al. ................. 623/17.12 |
| 2014/0288656 A1 | 9/2014 | Kuslich ....................... 623/17.16 |
| 2015/0057752 A1 | 2/2015 | Hibri et al. ................. 623/17.12 |

OTHER PUBLICATIONS

Sharma et al., "Manufacturing of Doubly Curved Tubular Composite Structures: Mapping and Weave Modifications", > Thermoplastic Composite Materials, 15:209-225 (May 2002).

Wu et al., The direct effect of graft compliance mismatch per se on development of host arterial intimal hyperplasia at the anastomotic interface, Annals of Vascular Surgery, 7(2):156-168 (Mar. 1993).

Viscocliosi et al., "Beyond Total Disc: The Future of Spine Surgery", Spine Non-Fusion, Musculoskeletal Investment Research, pp. 1-289 (May 2004).

International Search Report dated Jun. 25, 2014 for International Application No. PCT/US2014/019957, filed Mar. 3, 2014.

International Search Report dated Jun. 17, 2014 for International Application No. PCT/US2014/019911, filed Mar. 3, 2014.

International Search Report dated Jun. 19, 2014 for International Application No. PCT/US2014/019887, filed Mar. 3, 2014.

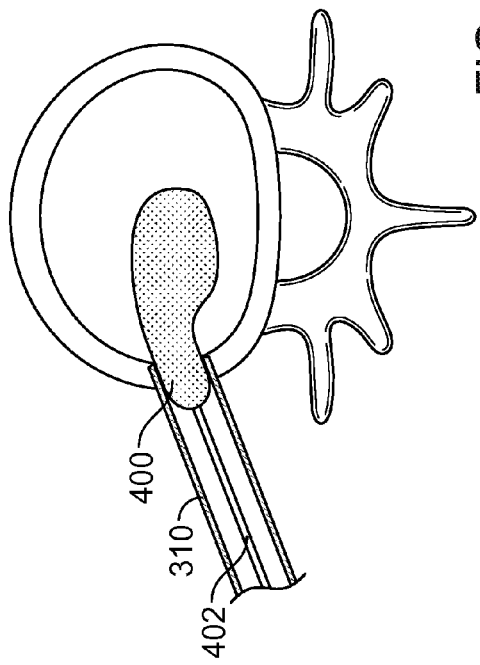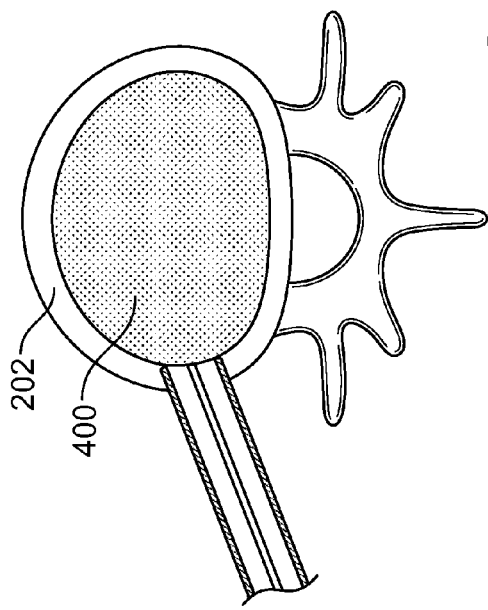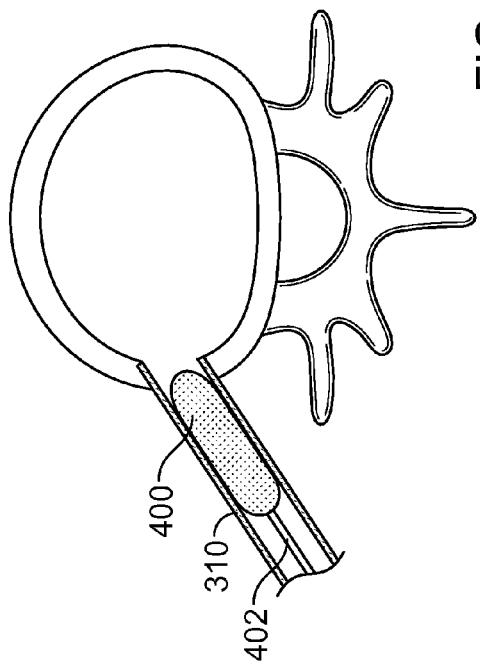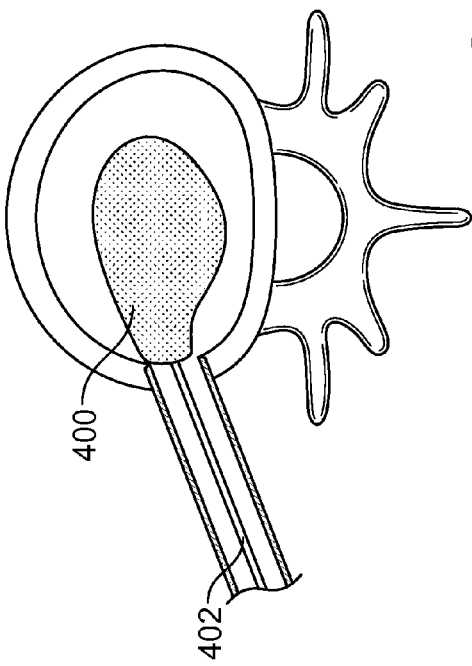

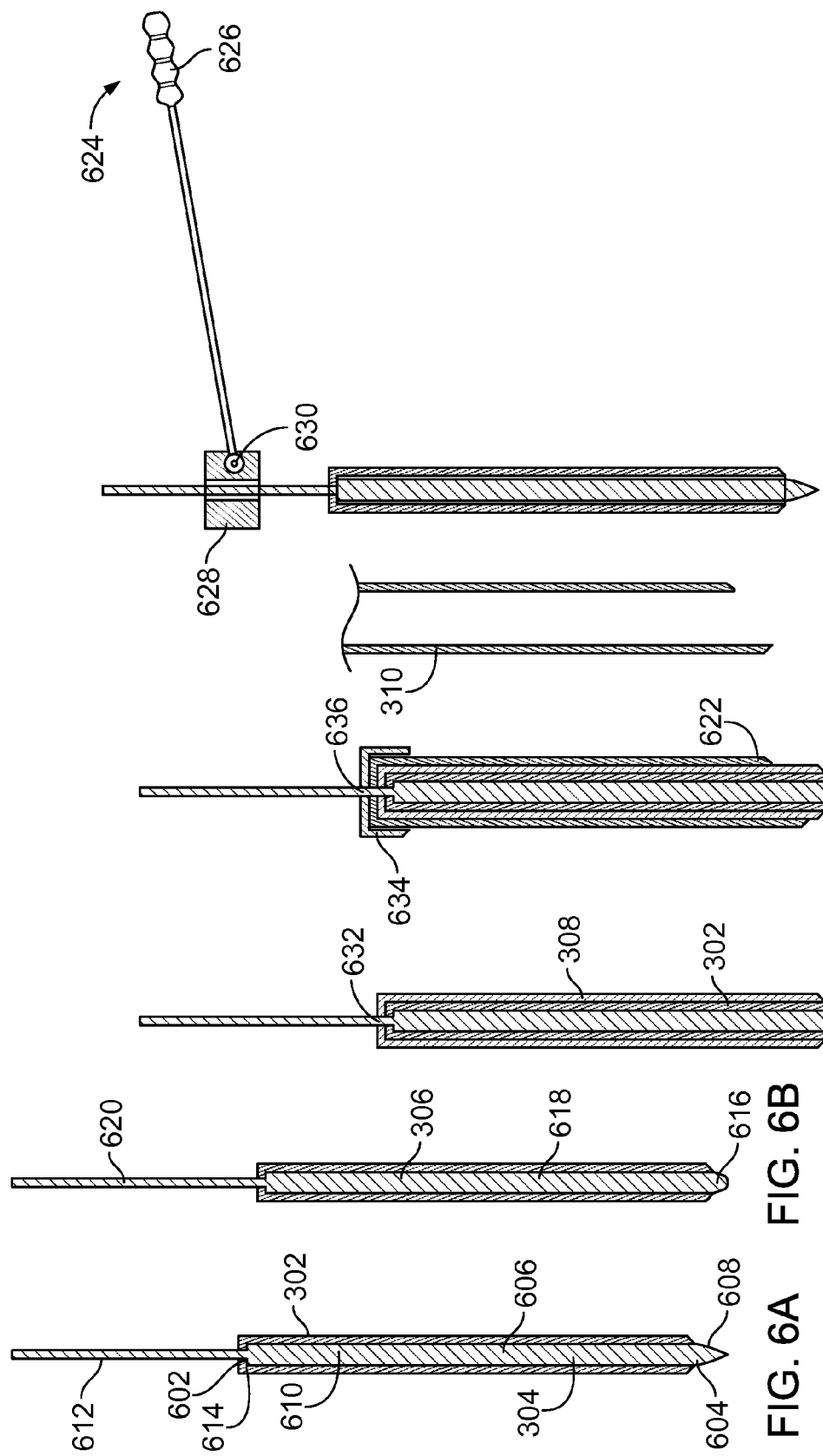

PROSTHETIC SPINAL DISK NUCLEUS

CROSS-REFERENCE TO RELATED APPLICATIONS

This application is a continuation of and claims priority to U.S. application Ser. No. 13/831,257, filed Mar. 14, 2013. The content of the prior application is incorporated herein by reference in its entirety.

TECHNICAL FIELD

This invention relates to surgically implanted devices, and more particularly to intervertebral disc prostheses.

BACKGROUND

The human vertebral column is a vital part of the human physiology that houses and protects the spinal cord, and provides structural support for the body. In a typical human, the vertebral column is made up of twenty-four articulating vertebrae and nine fused vertebrae, and is generally divided into several regions, including the cervical, thoracic, sacral, and coccygeal regions.

While variations exist between each vertebra depending on its location and region, vertebrae generally consist of a body, pedicles, a lamina, a spinous process, transverse processes, facet joints, and a spinal canal, each of which play a pivotal role in providing the overall supportive and protective functionality of the vertebral column. Of these features, the vertebral body is of particular importance in providing support. The vertebral body is the largest portion of the vertebra, provides an attachment point of intervertebral discs, protects the spinal cord, and bears the majority of the load of the vertebra.

Each vertebra is separated from an adjacent vertebra by an intervertebral disc, a cartilaginous joint that acts as a ligament to hold the vertebrae together. A disc consists of an outer annulus fibrosus which surrounds the inner nucleus pulposus. The annulus fibrosus consists of several layers of fibrocartilage which contain the nucleus pulposus and distribute pressure evenly across the disc. The nucleus pulposus contains loose fibers suspended in a mucoprotein gel. The nucleus of the disc acts as a shock absorber, absorbing the impact of the body's daily activities and keeping the two vertebrae separated.

While the interverbral disc protects adjacent vertebral bodies from impact or contact, various disorders may comprise the structure of the discs and negatively impact their functionality. For example, due to age, the nucleus pulposus may dehydrate and deform, or the annulus fibrosus may weaken and become more prone to tearing. Discs may also be damaged through trauma, resulting in undesirable bulging or loss of nucleus pulposus through a fissure. These disc disorders may diminish a disc's ability to absorb shock and transfer loads, or may cause adjacent vertebrae to contact, possibly resulting in acute or chronic pain for those suffering from these disorders.

To restore the functionality of a damaged or degenerated intervertebral disc, a common approach includes performing a discectomy to remove compromised material from within the intervertebral disc, and subsequently implanting a prosthesis in the void space created during the discectomy. The primary intention of these procedures is to ameliorate back pain by interrupting the vicious cycle that arises from abnormal spinal biomechanics and spinal instability, and by disrupting the cascade of reactive and degenerative processes of the bony and soft tissue. A secondary benefit is to limit the collateral damage to the spinal soft tissue envelope that is typical of traditional open spinal surgery and minimally invasive spinal surgery, thus diminishing postoperative pain and allowing earlier recovery.

So far, the methods and instrumentation required to achieve these goals have not been adequately developed or commercially available due to several deficiencies. First, existing methods and instrumentation have largely focused on total disc replacement, where the entirety of an intervertebral disc is removed and is replaced with a hinge-based prosthesis or a single-chambered disc-shaped inflatable structure. In these implementations, no attempt is made to preserve the annular fibrosis, which may be healthy despite degradation to the nucleus pulposus. Second, there is no existing method for the removal and replacement of intervertebral material, and the preservation of the annular fibrosis, that is performed entirely percutaneously.

Ideally, the treatment of intervertebral discs would involve a minimally invasive procedure, such that the discectomy and implantation process minimizes the disturbance of healthy surrounding tissue. Likewise, the tools and implants used during this process should be capable of minimally invasive deployment and operation. The implant should provide sufficient structural support to restore the functionality of an intervertebral disc, and should ideally preserve a significant degree of articulation freedom between vertebrae. The implant should also be resilient against sudden physical shocks and others external forces, such that it can withstand stresses seen during normal patient movement.

SUMMARY

This specification describes technologies relating to an intervertebral disc prosthesis used to strengthen and stabilize the spine. Implementations of the technology described herein comprise a surgical device that is implanted through a small surgical incision into a portion of a human intervertebral disc, various support tools used to insert such a surgical device, and a method by which the device is used to strengthen and stabilize the spine.

Various implementations of the present invention provide benefits that are desirable for surgical applications. The implantation of the device is minimally invasive, as it can be inserted and deployed within the body through a single small incision. As such, the implantation process results in minimal damage to healthy surrounding structures. The various tools used to deploy the device may also be deployed and operated through the same single incision, likewise minimizing collateral damage to healthy tissue. The device provides structural support to restore the functionality of an intervertebral disc, and also preserves a significant degree of articulation freedom between vertebrae. The device is also resilient against sudden physical shocks and others external forces, such that it can withstand stresses seen during normal patient movement.

One example embodiment of the present invention includes an implantable prosthetic device comprising: an inner chamber; an outer chamber fluidly isolated from the inner chamber; and a sealing valve in fluid communication with the inner chamber and the outer chamber, the sealing valve comprising a first sealing mechanism, a second sealing mechanism, and a stopper element. When the sealing valve is in an open state, the first sealing mechanism allows the inflow of a first material into the inner chamber and the second sealing mechanism allows the inflow of a second material into the outer chamber. When the sealing valve is in a closed state, the first sealing mechanism prevents outflow of the first material from within the inner chamber and the second sealing mechanism prevents outflow of the second material from within the outer chamber. A force applied the stopper causes the sealing valve to enter the open state; and the release of the force causes the sealing valve to enter the closed state.

One or more embodiments of the present invention include one or more of the following features: The first material comprises an inert gas. The second material comprises a silicone polymer. The silicone polymer is curable. The second material comprises an imaging contrast agent. An inflation device comprising a first channel and a second channel fluidly isolated from the first channel; wherein the inflation device is adapted to apply the force to the stopper, position the first channel in fluid communication with the inner chamber, position the second channel in fluid communication with the outer chamber, and simultaneously transfer the first material from the first channel to inner chamber and transfer the second material from the second channel to the outer chamber. The prosthetic device is collapsible. Inflating the inner chamber or the outer chamber with a material causes the prosthetic device to expand. The implantable device comprises a memory material, wherein the memory material expands the device to a pre-determined shape. The stylus and implantable device are adapted to fit into a surgical cannula. The device is adapted for use as an intervertebral disc prosthesis. The device is implanted to fit adjacent a first vertebra against an upper surface and a second vertebra against a lower surface, such that the first vertebra is separated from the second vertebra.

In yet another embodiment of the present invention, a method of implanting a prosthetic device comprises the steps of: penetrating the annular fibrosus; removing the nucleus pulposus; implanting an inflatable device within the annular fibrosus, wherein the inflatable device comprises an inner chamber, an outer chamber fluidly isolated from the inner chamber; and a sealing valve in fluid communication with the inner chamber and the outer chamber, the sealing valve comprising a first sealing mechanism, a second sealing mechanism, and a stopper element. When the sealing valve is in an open state, the first sealing mechanism allows the inflow of a first material into the inner chamber and the second sealing mechanism allows the inflow of a second material into the outer chamber. When the sealing valve is in a closed state, the first sealing mechanism prevents outflow of the first material from within the inner chamber and the second sealing mechanism prevents outflow of the second material from within the outer chamber. A force applied to the stopper causes the sealing valve to enter the open state; and the release of the force causes the sealing valve to enter the closed state.

In yet another implementation of the present invention an inflatable implantable device comprises an inflatable inner chamber and an inflatable outer chamber, wherein the outer chamber further comprises memory shape material adjacent the outer periphery capable of deforming from a first delivery shape, to a second, deployed shape; and an inflation valve in fluid communication with the inner and outer chamber and configured to receive and retain a first medium in the first chamber and a second medium in the second chamber. The inflation valve is configured to simultaneously inflate the first chamber with a first medium and the second outer chamber with a second medium.

In still a further implementation of the present invention, a method of providing cured silicon to the body comprises: implanting an inflatable containment element in the body; injecting a flowable, curable silicone into the containment vessel; and curing the injected silicone using either a curing agent or UV light. The implanted inflatable containment element is a balloon comprising an inner chamber fluidly isolated from an outer chamber, wherein the silicon is injected into at least one of the inner or the outer chambers.

In an additional implementation of the present invention, a method of providing cured silicone to the body comprises: creating a body cavity; injecting a flowable curable silicone into the body cavity; and curing the injected silicone using either a curing agent or UV light. The body cavity is made within a vertebral disc by removing the nucleus pulposus from within the annulus fibrosus; and wherein the silicone is injected within the annulus fibrosus. The silicone is injected freely into the annulus fibrosus or into a balloon within the annulus fibrosus.

In an further still embodiment of the present invention; a system for implanting an inflatable prosthetic vertebral nucleus comprises: an access and delivery cannula having an inner diameter, a nucleotomy tool for removal of the nucleus pulposus from a vertebral disc, wherein the nucleotomy tool is sized to fit within the inner diameter of the access and delivery cannula; a delivery and inflation stylus for delivering an inflatable prosthetic implant, wherein the stylus is sized to fit within the inner diameter of the access and delivery cannula; and an inflatable prosthetic disc implant comprising a first and second chamber, wherein the first and second chamber are fluidly isolated from one another, and the prosthetic disc implant is sized to be delivered through the access cannula by the delivery and inflation stylus to a position within the vertebral disc in an uninflated state.

And in an additional implementation of the invention a method for implanting an inflatable prosthetic vertebral nucleus, comprises: penetrating the annulus fibrosus and accessing the nucleus pulposus of an intervertebral disk using an access and delivery cannula; delivering through the access cannula a nucleotome that is configured to allow the removal of the nucleus fibrosis from the intervertebral disc while leaving the annulus fibrosus substantially intact; maneuvering the nucleotome within the intervertebral disc to remove the nucleus pulposus; removing the nucleotome; delivering a folded and deflated prosthetic implant through the access and delivery cannula and through the annulus fibrosus into the void formerly occupied by the nucleus pulposus; inflating the prosthetic implant using an inflation stylus wherein the prosthetic implant is inflated with at least two mediums including a gas and a curable silicon; curing the silicone within the prosthetic implant using a curing agent or UV light; and removing the inflation stylus and the access and delivery cannula.

In yet another implementation an access cannula for penetrating and accessing the annulus fibrosus of a vertebral disc comprises: a proximal end; a distal end; and an inner diameter sized to deliver one or more instruments or prosthetic devices; wherein the one or more instruments include a nucleotome, a delivery stylus, or an inflatable balloon. The proximal end is attachable to a light source. The inner diameter is sized to fit around one or more access dilators. The cannula further includes a set screw and adhesive set screw assembly.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 6A-F are cross-sectional views of exemplary surgical tools.

Like reference symbols in the various drawings indicate like elements.

DETAILED DESCRIPTION

The following description is of one exemplary embodiment of the invention. The description is not to be taken in a limiting sense, but is made for the purpose of illustrating the general principles of the invention. Various inventive features are described below that can each be used independently of one another or in combination with other features.

Broadly, this disclosure is directed at surgical tools for accessing the nucleus pulposus of an intervertebral disc and surgically implantable intervertebral disc prostheses.

Exemplary implementations of the present invention comprise various components of a surgical kit for accessing portions of the intervertebral disc, removing or displacing tissue, and delivering and implanting a prosthetic device. The kit in one exemplary embodiment comprises an access and delivery cannula, a nucleotomy tool for removal of the nucleus pulposus, a delivery and inflation stylus for delivering an inflatable prosthetic implant, and an inflatable prosthetic disc implant. An exemplary method of using an implementation of the present invention comprises penetrating the annulus fibrosus and accessing the nucleus pulposus of an intervertebral disk using an access and delivery cannula; delivering through the access cannula a nucleotome that is configured to allow the removal of the nucleus fibrosis from the intervertebral disc while leaving the annulus fibrosus substantially intact; maneuvering the nucleotome within the intervertebral disc to remove the nucleus pulposus; removing the nucleotome; delivering a folded and deflated prosthetic implant through the access and delivery cannula and through the annulus fibrosus into the void formerly occupied by the nucleus pulposus; inflating the prosthetic implant using an inflation stylus wherein the prosthetic implant is inflated with at least two mediums including a gas and a curable silicon; and removing the inflation stylus and the access and delivery cannula.

Various aspects of the present invention, for example, a surgical tool for removing tissue from the body, such as removing nucleus pulposus from an intervertebral disc are disclosed in U.S. patent application Ser. No. 13/831,355, entitled "Surgical Device", filed concurrently with this application and incorporated herein by reference in its entirety. Broadly the tool includes an access and delivery cannula through which a nucleotome can be delivered. The nucleotome includes one or more passages to provide irrigation, suction and a flexible agitation tool.

Other aspects of the present invention, including an example inflatable prosthetic implant are disclosed in U.S. Patent Application Pub. No. US 2010/0256766, entitled Percutaneous Implantable Nuclear Prostheses and filed, Apr. 2, 2010, is incorporated herein by reference in its entirety.

Figure 1:
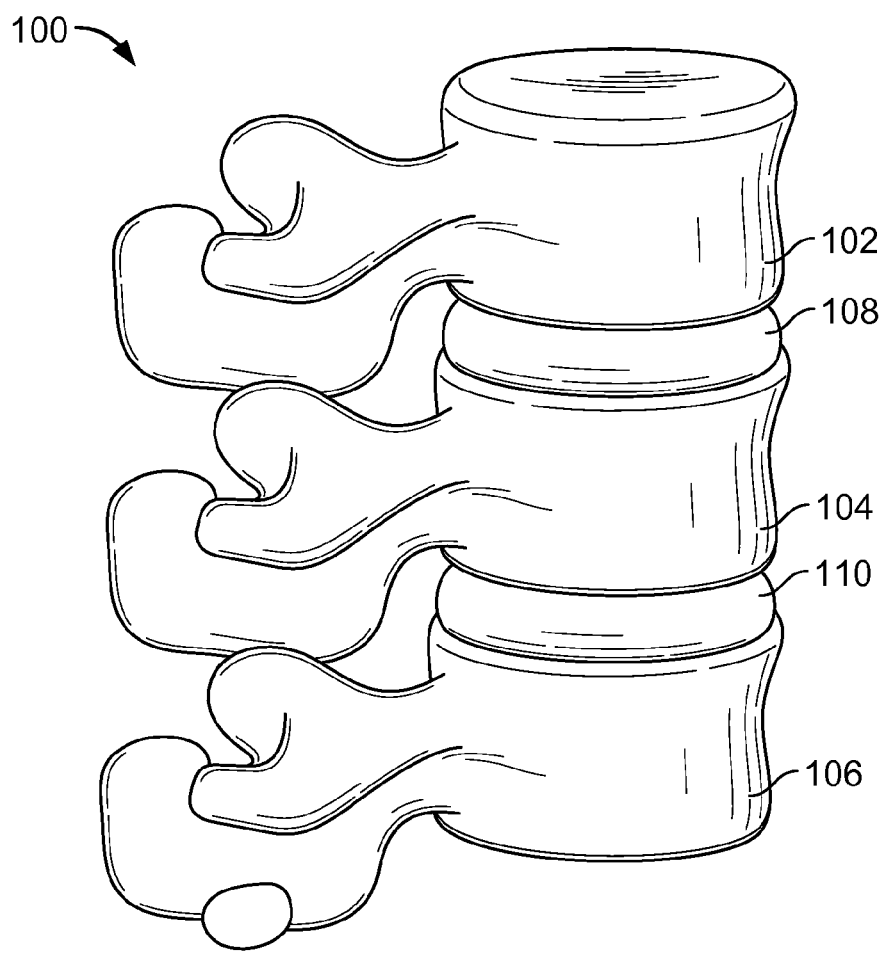
FIG. 1 is a perspective view of a portion of a human vertebral column.
Figure 2:
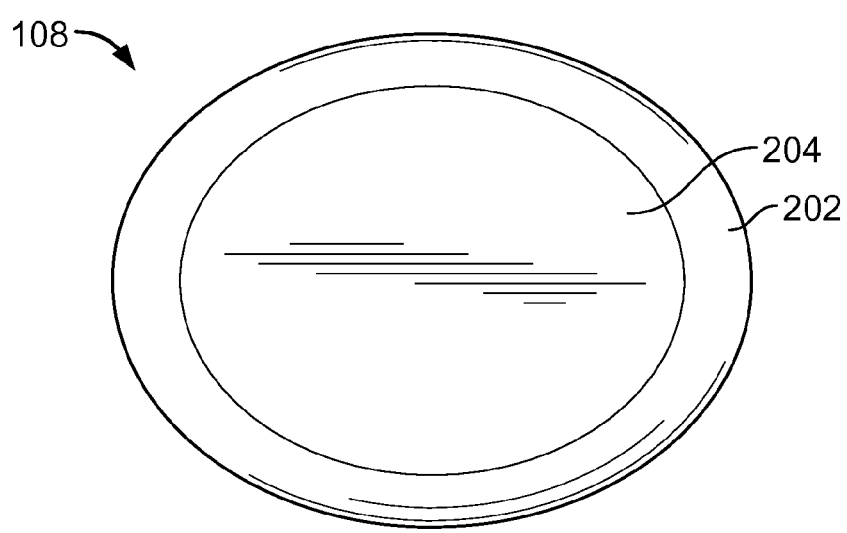
FIG. 2 is a cross-sectional view of a human intervertebral disc.

FIGS. 1 and 2 illustrate a portion of a typical human vertebral column. A vertebral column 100 is made up of several vertebral bodies 102, 104, and 106 separated by intervertebral discs 108 and 110. Intervertebral disc 108 is made up of an annular fibrosis 202 surrounding a region of nucleus pulposus 204.

Figure 3:
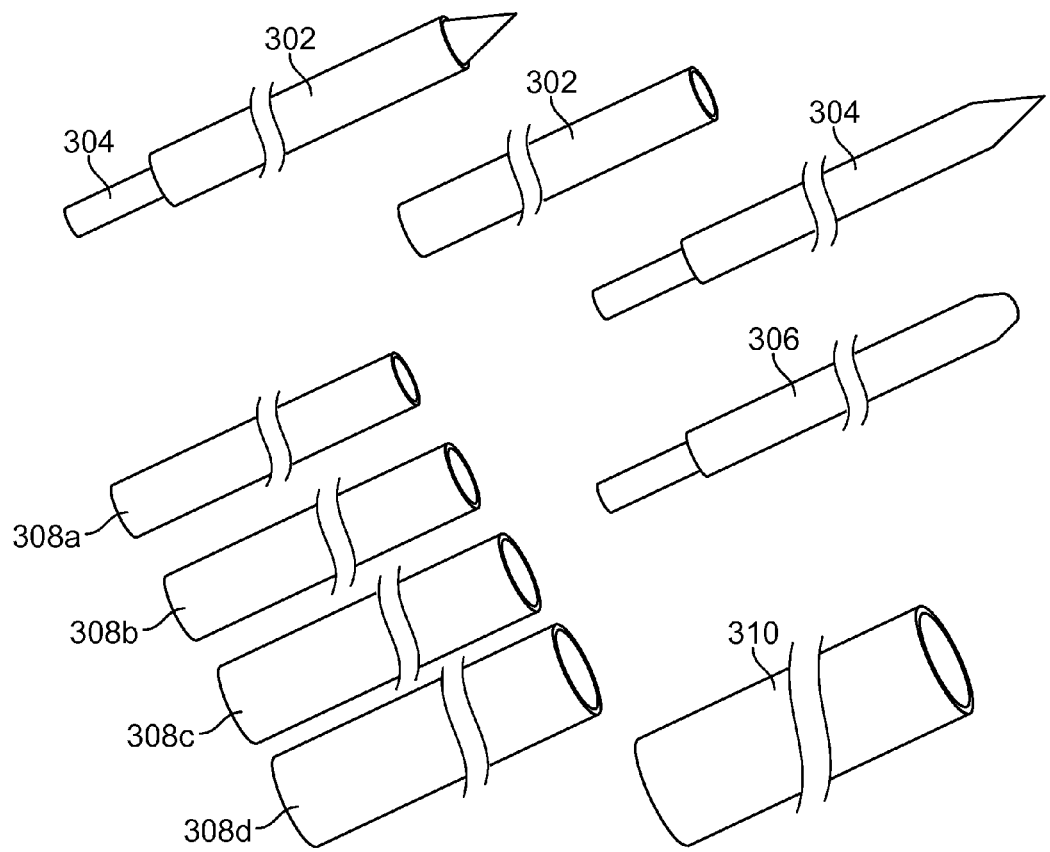
FIG. 3 is a perspective view of exemplary surgical tools.

FIG. 3 illustrates exemplary surgical tools used to access the nucleus pulposus of an intervertebral disc. Tools include guide sleeve 302, guide pin 304, obturator 306, several dilators 308a-d, and outer cannula 310.

Figure 4:
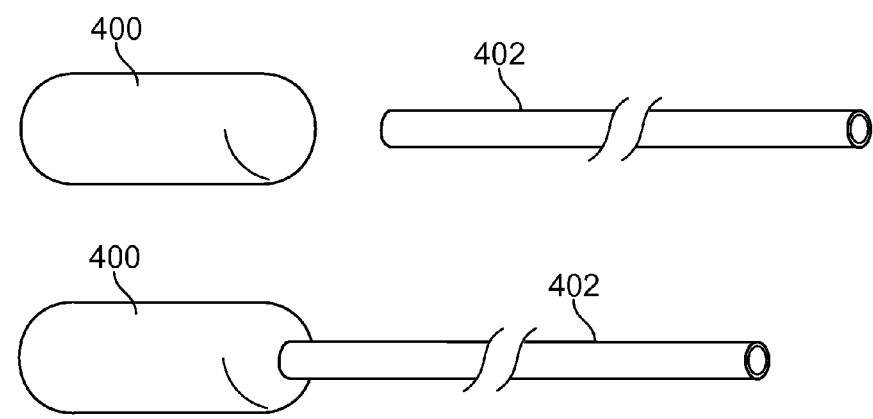
FIG. 4 is a perspective view of an exemplary implant device.

FIG. 4 illustrates an exemplary implant device 400 and inflation stylus 402. Implant device 400 may be attached to inflation stylus 402.

FIG. 5 illustrates an exemplary method of use of tools 302, 304, 306, 308 and 402 to insert implant device 400 through the annulus fibrosis 202 of intervertebral disc 108, and deploy implant device 400 as an intervertebral disc prostheses.

Figure 5A:
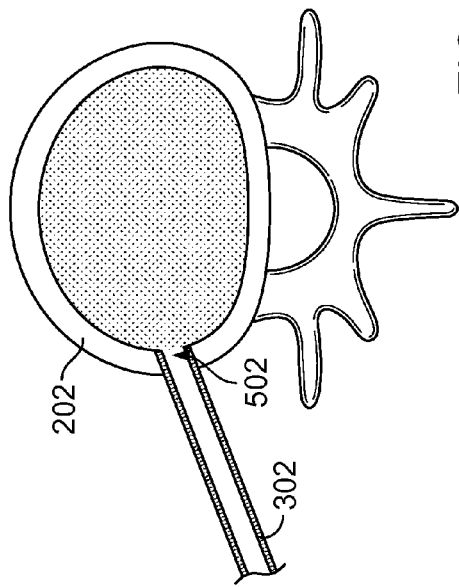
FIGS. 5A-N illustrate an exemplary method of use including the surgical tools and implant device.

Referring to FIG. 5A, guide pin 304 is slideably inserted into guide sleeve 302, and guide sleeve 302 and guide pin 304 are inserted through the skin of a patient in a prone position. Guide sleeve 302 and guide pin 304 enter the patient's body in an oblique postero-lateral approach. Force is applied to guide sleeve 302 and guide pin 304 until the leading tip of guide pin 304 pierces annular fibrosis 202, creating aperture 502.

Figure 5B:
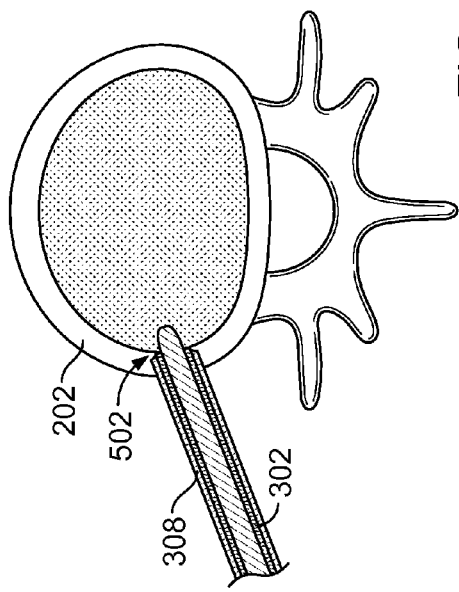

Referring to FIG. 5B, guide pin 304 is slideably withdrawn from guide sleeve 302. Guide sleeve 302 remains in its inserted position, sustaining aperture 502 of annular fibrosis 202.

Figure 5C:
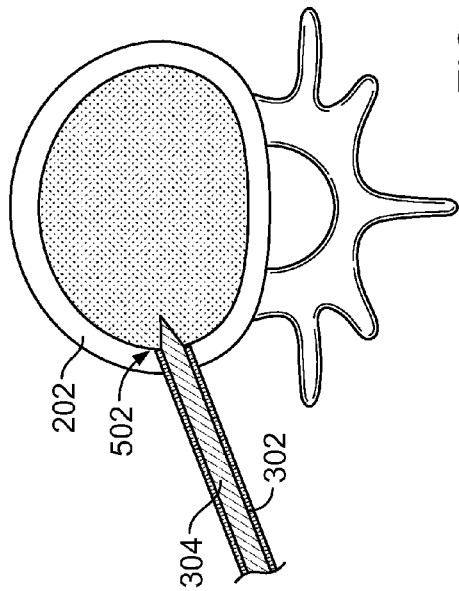

Referring to FIG. 5C, obturator 306 is slideably inserted into guide sleeve 302, such that the leading tip of obturator 306 extends out of guide sleeve 302, through annular fibrosis 202 and aperture 502, and into nucleus pulposus 204.

Figure 5D:
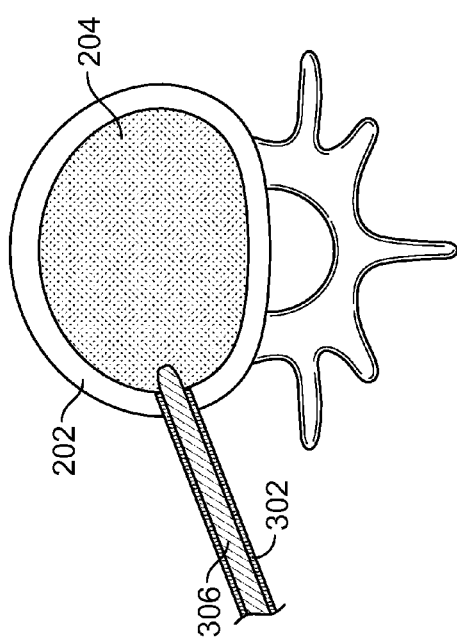

Referring to FIG. 5D, dilator 308 is inserted telescopically around guide sleeve 302 until its distal end reaches the distal margins of the annulus fibrosis 202, widening aperture 502. Several dilators 308 of increasingly larger diameters may be telescopically inserted in succession to gradually widen aperture 502.

Figure 5E:
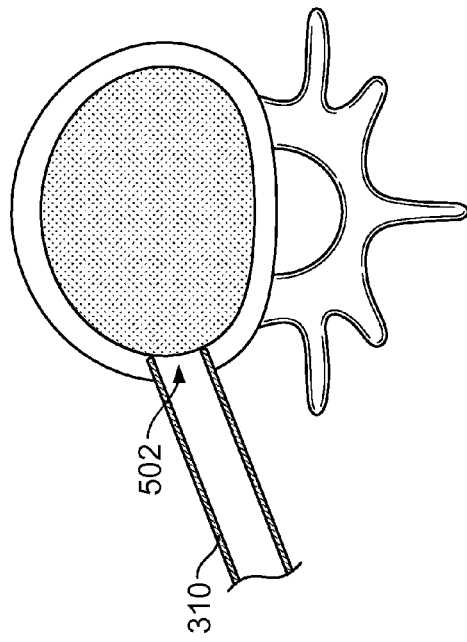

Referring of FIG. 5E, when aperture 502 is widened to the desired size, outer cannula 310 is telescopically inserted around the dilators 308. Similar to the insertion of dilators 308, outer cannula 310 is advanced until its distal end reaches the distal margins of the annulus fibrosis 202.

Figure 5F:
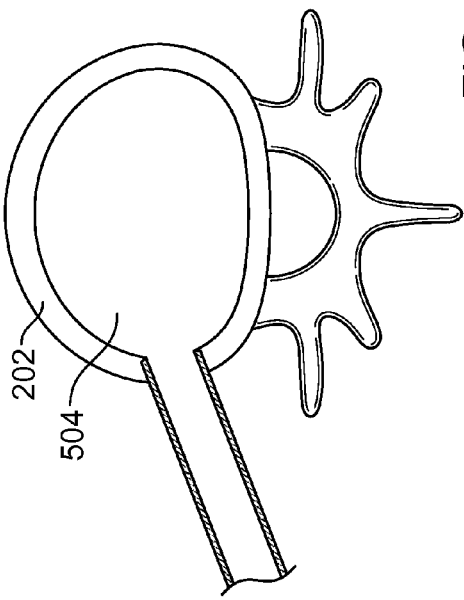

Referring to FIG. 5F, guide sleeve 302, obturator 306, and dilators 308 are slideably withdrawn from within outer cannula 310. Outer cannula 310 remains in its inserted position, sustaining aperture 502 in a dilated state.

Figure 5G:
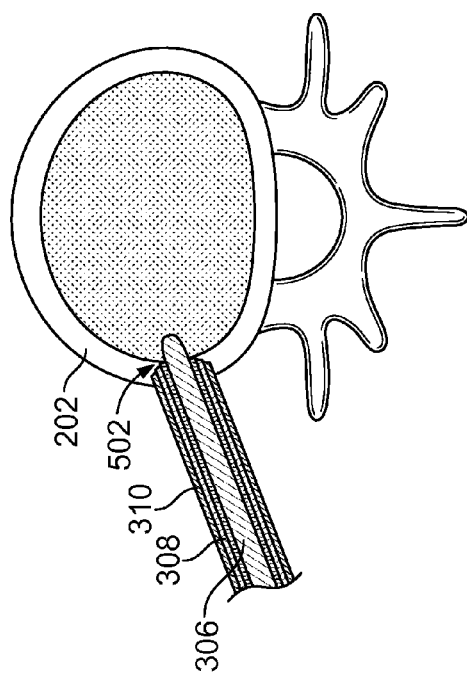

Referring to FIG. 5G, nucleus pulposus 204 is removed through outer cannula 310. Removal may be through a vacuum suction applied to outer cannula 310, or through a separate nucleus pulposus removal tool (not shown) that is inserted into outer cannula 310 and operated within annular fibrosis 202.

Figure 5H:
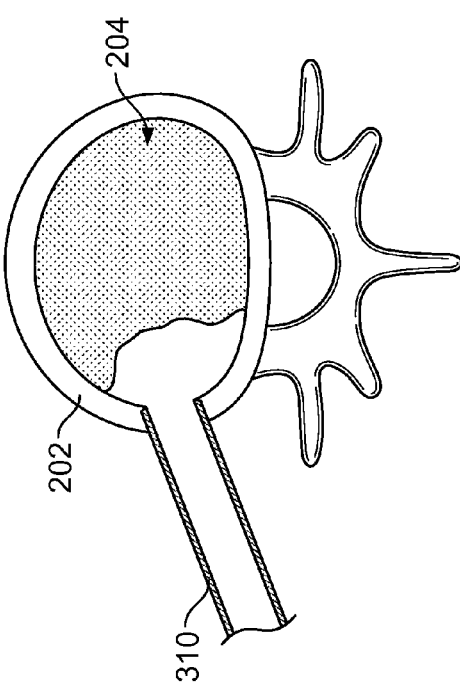

Referring to FIG. 5H, after nucleus pulposus 204 is removed, a void 504 is created within annular fibrosis 202.

Referring to FIG. 5I, implant device 400 and inflation stylus 402 are inserted into outer cannula 310.

Referring to FIG. 5J, force is applied to inflation stylus 402 to push implant 400 into void 504.

Referring to FIG. 5K, implant device 400 is filled with a gas or other material passed through inflation stylus 402. This inflates implant device 400, expanding it in size.

Referring to FIG. 5L, when implant device 400 is fully inflated, implant device fills a portion of or the entirety of void 504, and directly abuts the inner circumference of annular fibrosis 202.

Figure 5N:
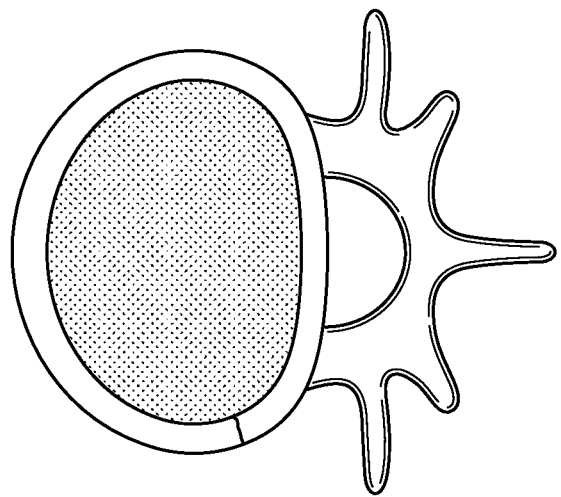
Figure 5M:
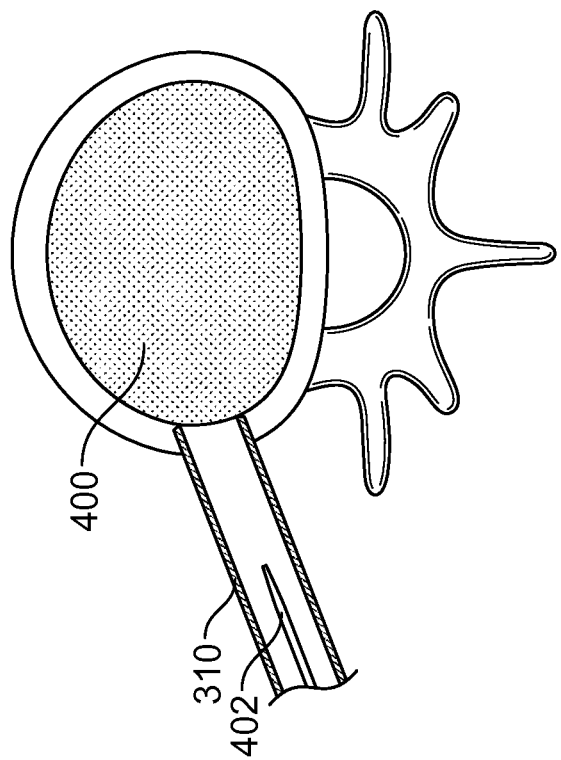

Referring to FIG. 5M, inflation stylus 402 is detached from 400 and withdrawn through outer cannula 310.

Referring to FIG. 5N, outer cannula 310 is withdrawn, leaving implant device 400 positioned within annular fibrosis 202. Annular fibrosis retracts, closing aperture 502.

During this process, the position of each of the tools and implants may be tracked and guided through imaging observation techniques typical in the field of interventional radiology. Imaging modalities may include fluoroscopy, magnetic resonance imaging (MRI), computed tomography (CT), X-ray imaging, positron emission tomography (PET), or other medical imaging technique. During this process, imaging may be conducted alongside the implantation procedure, such that progress may be tracked in real-time.

As this process is conducted predominantly through narrow access channels created by guide sleeve 302 and outer cannula 310, and may be externally observed through common interventional radiology techniques, this process is minimally invasive to the patient. This process may be carried out under local anesthesia and under conscious sedation, thus avoiding the risk of general anesthetics. Alternatively, these techniques may also be utilized in conjunction with more invasive techniques, and need not be limited in application.

Moreover, as no portion of annular fibrosis 202 is excised from the body during this process, this technique is minimally traumatic to the patient. In particular, healing of the annular fibrosis is rapid compared to techniques requiring the excision of annular fibrosis tissue, and the preservation of the annular fibrosis structure limits the loss of intra-discal pressure, improving a patient's long-term recovery.

FIG. 6 illustrates in greater detail the various tools described above. Referring to FIG. 6A, guide sleeve 302 is generally an axially extending tube of uniform diameter, defining aperture 602 on its proximal end and aperture 604 on its distal end and a channel 606 between. Guide sleeve 302 includes an annular shoulder 614 at its proximal end. Guide sleeve 302 is generally of an ovular cross section, but may alternatively have a circular, ovular, obround, square, polygonal, or irregular cross-section.

Guide pin 304 is shaped to correspond to channel 606, and may be slideably inserted into guide sleeve 302. Guide pin 304 includes a sharpened tip 608, a body portion 610, and a tail portion 612. Tip 608 is pointed to allow for insertion into the annular fibrosis 202, as may be of a conical, beveled, or other such shape. Tail 612 is generally reduced in cross-sectional size compared to body 610, such that when guide pin 304 is fully inserted into guide sleeve 302, tail 612 passes through aperture 606. In this configuration, guide pin body 610 abuts shoulder 614, restricting the movement of guide pin 304.

Guide pin 304 may slideably removed from within guide sleeve 302 and replaced with obturator 306, as illustrated in FIG. 6B. Obturator 306 is generally similar in shape and dimensions to guide pin 304, but has a dulled tip 616. Obturator 306 likewise includes a tail portion 620 that is generally reduced in cross-sectional size compared to a body portion 618 and adapted to pass through aperture 602.

Dilator 308 may be telescopically inserted around the exterior of guide sleeve 302, as illustrated in FIG. 6C. Dilator 308 is generally similar in shape to guide sleeve 302, but is wider in diameter to fit snuggly around the exterior surface of guide sleeve 302. Several dilators 308 of successively larger cross-sectional diameters may be sequentially inserted to increase the overall diameter of the nested tools. Each dilator 308 includes a shoulder with an aperture 632, through which the tail portion 620 of obturator 306 may pass.

When the desired number of dilators 308 have been nested around guide sleeve 302, outer cannula 310 is telescopically inserted around the outermost dilator 308, as illustrated in FIG. 6D. Outer cannula 310 is generally similar in shape to case sleeve 302 and dilators 308, and is shaped to fit snuggly around the exterior surface of the outermost dilator 308. However, outer cannula 310 does not have a shoulder region on its proximal tip. On its distal tip, outer cannula defines aperture 622. Aperture 622 is obliquely positioned to correspond to an oblique postero-lateral approach into the annular fibrosis, and to allow for guidance of tools in a transverse orientation. Depending on the desired direction of tool guidance, the size and orientation of aperture 622 may be varied. For example, in some embodiments, aperture 622 is not obliquely positioned, and is instead positioned along the longitudinal extension of outer cannula 310. In other embodiments, aperture 622 is positioned orthogonal to the longitudinal extension of the outer cannula. In some embodiments, the tip of outer cannula 310 may include a slanted redirecting element such as a curved or inclined surface. This surface may be concave to conform to the convex surfaces of an inserted tool or device.

The user may also place a cap 634 over dilators 308 and outer cannula 310 to ensure that unwanted material does not fall until aperture 624. Cap 634 is a generally in the shape of an edged annulus with an aperture 636. Guide pin tail 612 or obturator tail 620 may fit through aperture 636, such that cap 634 may be slideably placed or removed from its installed position over outer cannula 310 or dilators 308.

As outer cannula 310 does not have a shoulder region, obturator 306, guide sleeve 302, and the one or more dilators 308 may be separated from outer cannula 310 by lifting tail portion 620 of obturator 306, as illustrated in FIG. 6E.

In this manner, the above tools are used to form a gradually widening aperture into an intervertebral disc and are then removed, leaving an outer cannula 310 to maintain the aperture at a desired dilated size and to provide external access for other tools or devices.

A hammer 624 may be used to position drive tools 302, 304, 306, 308, and 310 within the patient. Hammer 624 includes a handle 626, an annular contact element 628, and a hinge element 630. Contact element 628 is adapted to fit around guide pin tail 612 or obturator tail 620, and may be used to strike a tool in order to drive it deeper into the operating region. Hinge 630 allows handle 626 to rotate relative to 628 such that handle 626 may be swung without altering the orientation of striking element 628.

Each of tools 302, 304, 306, 308, and 310 are generally of an ovular cross section, but may alternatively have a circular, ovular, obround, square, polygonal, or irregular cross-section. Generally, tools 302, 304, 306, 308, and 310 are made of surgically compatible materials, such that they can be safely used in a sterile environment. Some portions of tools 302, 304, 306, 308, and 310 may be made of a radiopaque material, such that they provide imaging contrast during x-ray or fluoroscopic procedures. Some portions of tools 302, 304, 306, 308, and 310 may be made of non-ferrous materials, such that they are usable in conjunction with magnetic resonance imaging. Portions of tools 302, 304, 306, 308, and 310 may be made of paramagnetic or super paramagnetic materials, such that they provide imaging contrast during MRI.

Figure 7A:
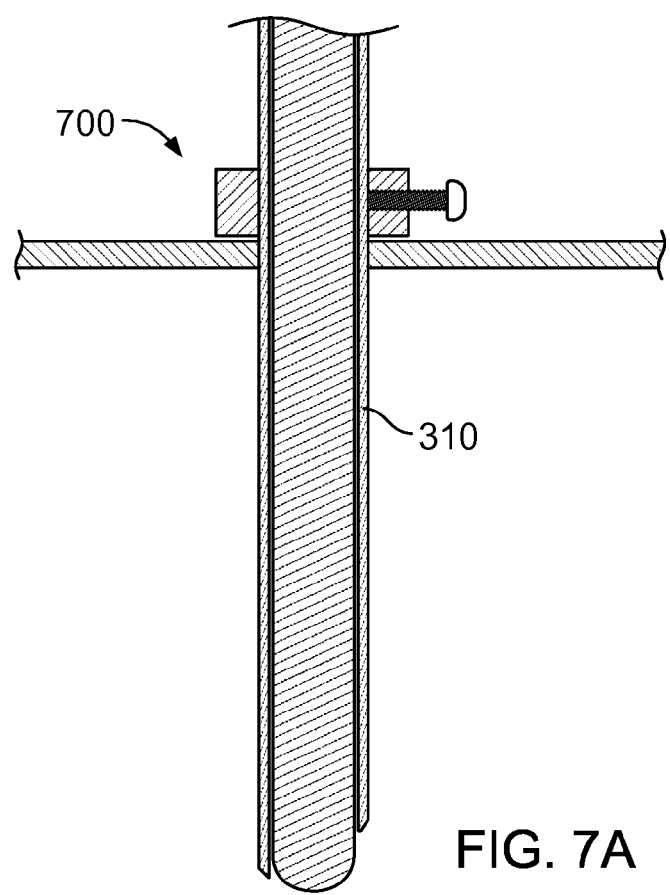
FIGS. 7A-B are cross-sectional views of an exemplary tool anchor.
Figure 7B:
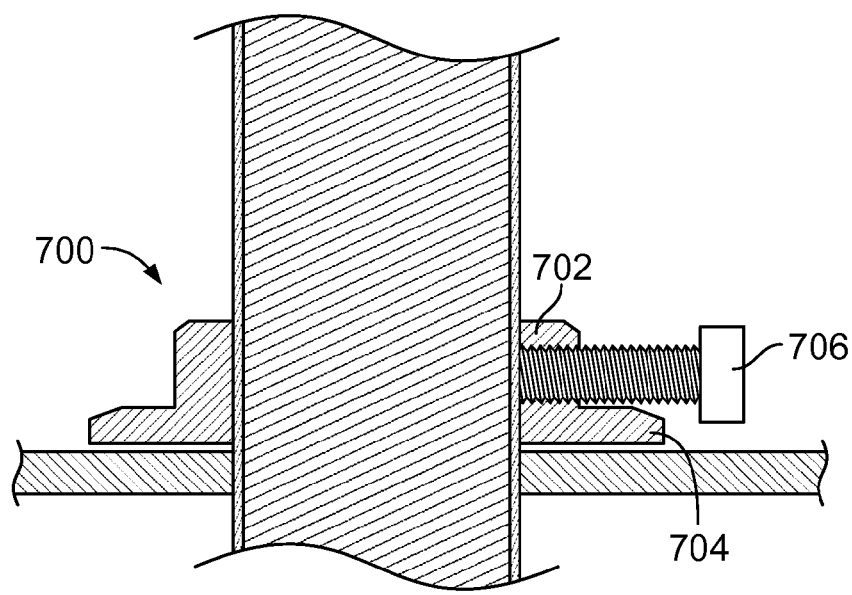

Tools 302, 304, 306, 308, and 310 may be anchored to the exterior of the patient to prevent shifting. As illustrated in FIG. 7A, anchor 700 is positioned on the exterior of the patient to grip a tool, for instance outer cannula 310. Referring to FIG. 7B, retaining ring includes an annular retaining ring 702 shaped encircle the exterior surface of a tool. Retaining ring 702 includes a lower flange 704, which may be coated with an adhesive to firmly attach anchor 700 to the patient's skin. An adjustment screw 706 is provided to adjustably secure the tool to anchor 700. Turning the adjustment screw 706 compresses the retaining ring 702 around the tool, tightly gripping the tool in position. Turning the adjustment screw in the opposite direction releases the tool, allowing either anchor 700 or the tool to be removed or repositioned. As the nested tools widen in diameter, for instance if several dilators are telescopically inserted one after another, adjustment screw 706 may be used to gradually widen retaining ring 702 to secure each new tool. Adjustment screw 706 may be of a captive design, such that it cannot be removed from retaining ring 702 after becoming fully unscrewed. In some embodiments, adjustment screw 706 may be replaced by a pin or a latch. In some embodiments, retaining ring 702 may be tightened by a ratcheting mechanism or other similar fastener.

Figure 8:
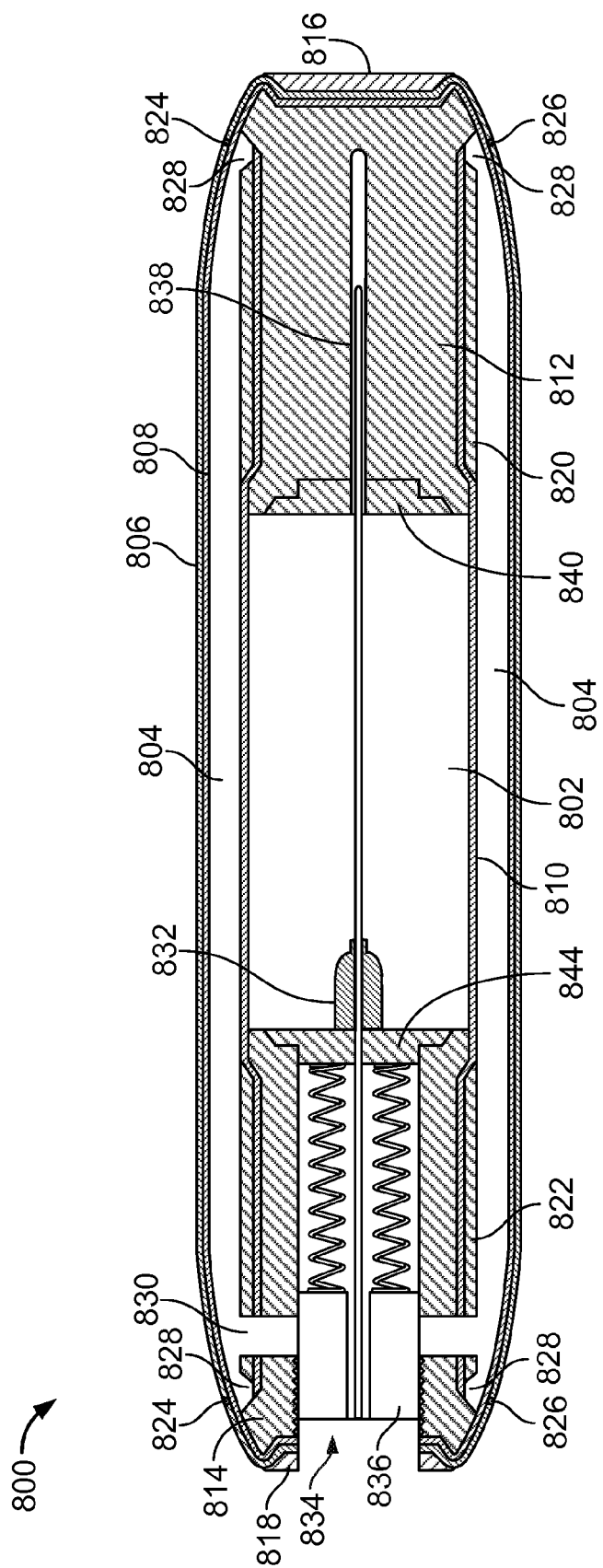
FIG. 8 is an overhead cross-sectional view of an exemplary implant device.

FIG. 8 illustrates an embodiment of implant device 400 in greater detail. Shown from an overhead cross-sectional view, implant device 400 is generally an obround cylinder with two major chambers: a centrally located inner chamber 802 and annular outer chamber 804. Inner chamber 802 is distinct from outer chamber 804, such that substances contained in one chamber cannot pass into the other chamber.

Chambers 802 and 804 are defined, in part, by outer body layers 806 and 808, inner body layer 810, and support bodies 812 and 814. Outer body layers 806 and 808 are secured to forward support body 814 by a crimp element 818, and to rear support body 812 by a crimp element 816. Inner body layer 810 is secured to forward support body 814 by a crimp element 822 and to rear support body 816 by a crimp element 820.

Layers 806, 808, and 810 may be formed of any durable material that is adequately firm, pliable, and resilient, such as silicone or a bio-compatible textile. Each layer should allow for deformation, such that if chambers 802 and 804 are inflated, layers 806, 808, and 810 can deform, expanding the outer dimensions of device implant 400. Each layer may be made of the same material, or may each be made of a different material in order to provide various benefits. For instance, layer 806 made be made of a bio-compatible textile, such that the outermost surface of implant device 400 is resistant against tears and punctures, while layer 808 may be made of a different material, such as silicone, to provide a softer, more compliant containment layer for chamber 804.

In some embodiments, layers 806 and 808 are affixed along a portion to the entirety of each layer. In some embodiments, layer 806 and 808 may be fixed together or to other portions of device 400 with an adhesive, with thread, or with other such attachment mechanisms.

Figure 9:
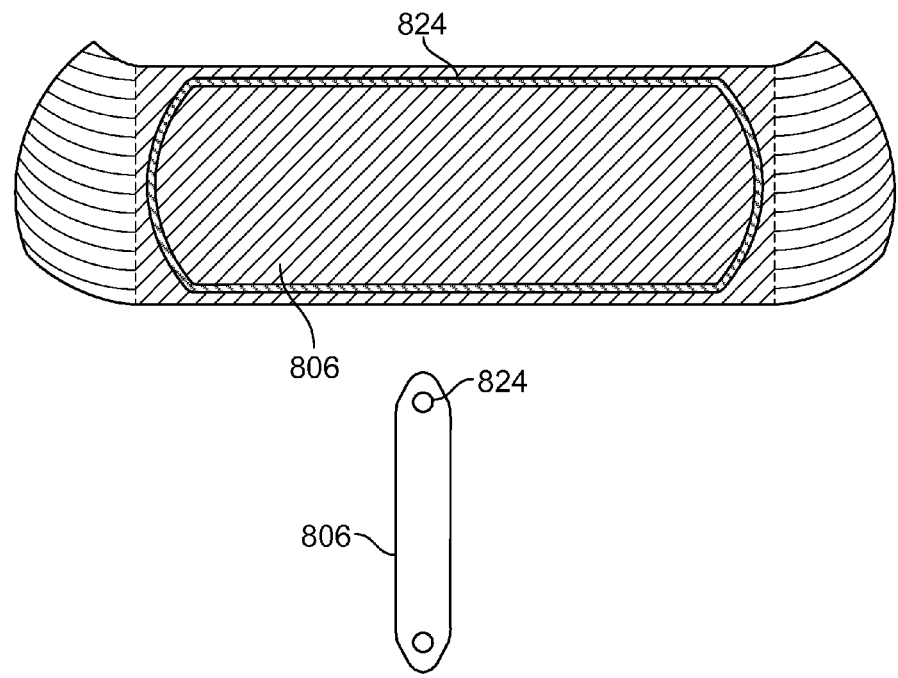
FIG. 9 is a side view of an exemplary implant device.

Outer body layer 806 also includes support wires 824 and 826, for example as illustrated in FIGS. 8 and 9. FIG. 9 illustrates a side view of implant device 400 with support wire 824 embedded in outer body layer 806. Support wires 824 and 826 are typically of a biocompatible memory metal, such nitinol, such that outer body layers 806 and 808 may be pressed against inner body layer 810 when chamber 804 is empty (for instance when implant device 400 is loaded into a delivery cannula), but will expand to a pre-determined shape when released (for instance when implant device 400 is expelled from a delivery cannula is positioned within an intervertebral disc). Pre-determined shapes may include, for example, a three-dimensional convex shape corresponding to the inner surface of an annular fibrosis. Several notches 828 provide seating room for support wires 824 and 826, such that outer body layers 806 and 808 can seat flush against inner body layer 810. In some embodiments, wires 824 and 826 are embedded in layer 806. In some embodiments, wires 824 and 826 are instead positioned on the surface of layer 806 and attached to layer 806 by various attaching mechanisms, such as adhesive or thread. In some embodiments, wires 824 and 826 are attached by passing between each wire repeatedly between the inner and outer surfaces in a stitch-like pattern.

Generally, support bodies 812 and 814 are also made of a firm, pliable and resilient materials. Typically, support bodies 812 and 814 are of a firmer material than that of layers 806, 808, and 810 in order to provide added structural support for implant device 400. For example, support bodies 812 and 814 may be made of a stiffer silicone polymer that is more resistant against externally applied forces. However, support bodies 812 and 814 need not be made of a stiffer material than layers 806, 808, and 810, and the stiffness and resilience of these materials may be varied to achieve the desired physical characteristics.

Inner chamber 802 is additionally defined by forward wall 844 and rear wall 840. Walls 844 and 840 abut forward support body 814 and rear support body 812, respectively, creating an air-tight and liquid-tight seal. Walls 844 and 840 may be secured to each support body in various ways, for example a notched arrangement, as illustrated in FIG. 8. Walls 844 and 840 may be alternatively or additionally secured using other mechanisms, for example with an adhesive, weld, crimp, or thread. Walls 844 and 840 may also instead be integral with each support body, such that a securing mechanism is not required. Walls 844 and 840 are generally of a firm material, such as a dense silicone polymer, such that the general shape of walls 844 and 840 are preserved under the application of external force. However, the materials of walls 844 and 840 may also be varied to achieve a desired stiffness and resilience.

When implant device 400 is positioned within an intervertebral disc, chambers 802 and 804 may each be inflated with various substances to increase the physical dimensions of implant device 400 and to provide prosthetic support. Inflation substances may pass from a cylindrical fill channel 834 into outer chamber 804 through aperture 830. One or more apertures 830 are defined through forward support member 814, inner body layer 810, and crimp 822, and provide fluid communication between fill channel 834 and outer chamber 804.

Figure 10:
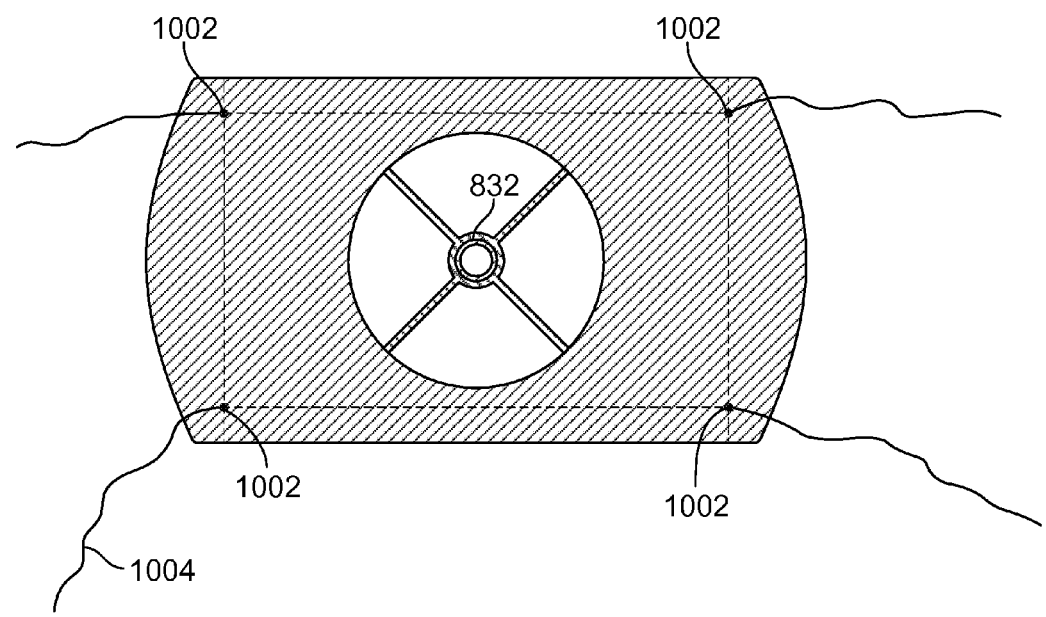
FIG. 10 is a front view of an exemplary implant device.

Inflation substance may pass from fill channel 834 into inner chamber 802 through valve 832. As illustrated in FIG. 8, valve 832 may be of a self-sealing design, such that pressure from within inner chamber 802 seals valve 832. In some embodiments, valve 832 may be integral with wall 844. Alternatively valve 832 may be a separate element, as illustrated in FIG. 10. In these embodiments, valve 832 may be secured to wall 844 in various ways, such as through an adhesive, weld, or thread. When secured with thread, one or more thread holes 1002 may be positioned along the faces of wall 844 and valve 832, such that a securing thread 1004 may be used to tie wall 844 and 832 together. Valve 832 may be made of various materials, such as a rubber or silicone polymer.

Figure 11A:
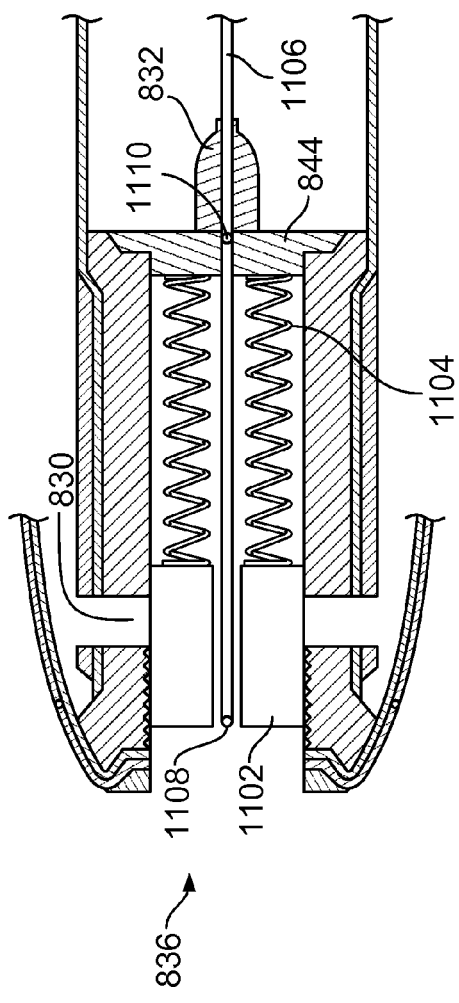
FIGS. 11A-B are detailed cross-sectional views of an exemplary dual-valve structure.

Inflation of implant device 400 is regulated by dual-valve structure 836 positioned within fill channel 834. Dual-valve structure 836 is illustrated in greater detail in FIG. 11. Dual-valve structure 836 includes an annular stopper 1102 attached to spring element 1104 and fill tube 1106. Fill tube 1106 extends from fill channel 834 to a channel 838 defined within rear support member 812, and has two apertures 1108 and 1110. In its sealed state, as illustrated in FIG. 11A, spring elements 1004 force stopper 1110 away from wall 844, sealing aperture 830 and valve 832. In this state, no substance may enter or exit chambers 802 and 804. In some embodiments, there may be one or more spring elements 1004. In some embodiments, multiple spring elements 1004 may be arranged to evenly apply force to stopper 1110.

Figure 11B:
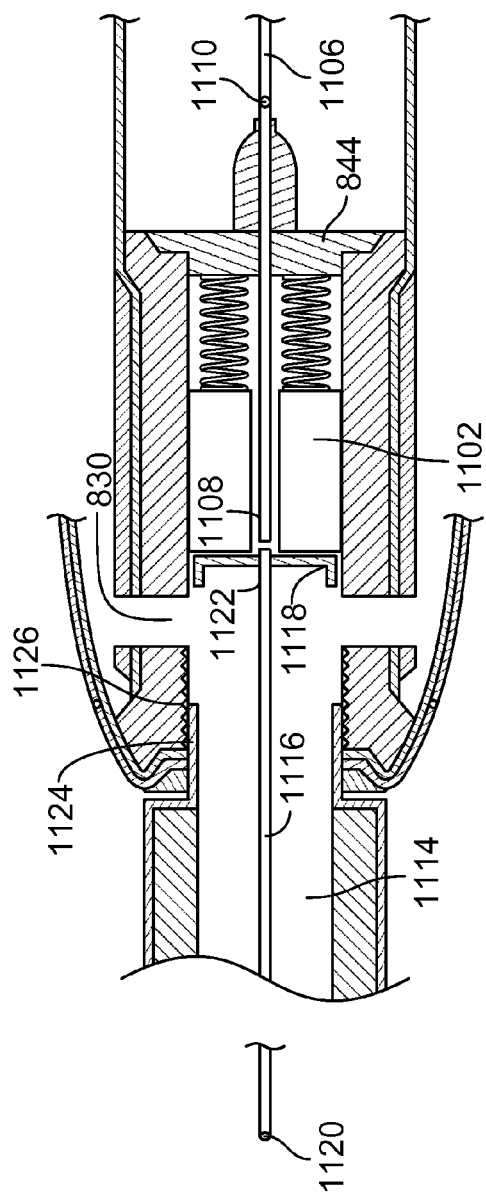

Dual-valve structure may be opened by pressing stopper 1102 against the force of spring elements 1004, as illustrated in FIG. 11B. In this open state, stopper 110 is pushed towards wall 844, unblocking aperture 830. In addition, as stopper 110 is pushed toward wall 844, fill tube 1106 is pushed, moving fill tube 1106 along through valve 832 and channel 838 until aperture 1110 passes out of valve 832 and into inner chamber 802. Thus, in this open state, valve 832 is opened and substances may pass from fill channel 834 into inner chamber 802 through apertures 1108 and 1110.

A suitably dimensioned fill stylus 402 may be used to simultaneously open dual-valve structure 836 and inflate implant device 400. The leading tip of an example embodiment of fill stylus 402 is illustrated in greater detail in FIG. 11B. Fill stylus 402 is generally tubular and includes a fill needle 1116 positioned within channel 1114, and an annular plunger 1118 affixed to fill needle 1116. Fill needle 1116 is tubular with apertures 1120 and 1122, and is otherwise air-tight and liquid-tight. As such, substances contained within fill needle 1116 remain separated from substances contained within channel 1114. Fill stylus 402 also includes external threads 1124 corresponding to internal threads 1126 of fill channel 834. Thus, fill stylus 402 may be attached to implant device 400 by screwing fill stylus 402 into fill channel 834. As fill stylus 402 is screwed in, plunger 1118 advances, pushing stopper 1102 against wall 844 and revealing aperture 830 to channel 1114. In addition, fill needle aperture 124 abuts dual-valve structure aperture 1108, providing gaseous or fluid communication between fill needle 1116 and inner chamber 802. Substances from channel 1114 and fill needle 1116 may then be passed into chamber 804 and chamber 802, respectively, inflating implant device 400. This may be accomplished, for example, using a motorized pump system, a manually operated pump, or a syringe mechanism. Pumping of each substance within fill stylus 402 may be controlled simultaneously or individually, such that the filling of each chamber 802 and 804 may be simultaneously or individually regulated.

After implant device 400 has been inflated, fill stylus 1112 is unscrewed, returning dual-valve structure 836 to its closed state and sealing chambers 802 and 804. In some embodiments, dual-valve structure 836 also includes one or more bosses or protuberances on the surface of stopper 1102, corresponding to apertures 830. When stopper 1102 sides from an open position to a closed position, the bosses may engage with aperture 830, securing stopper 1102.

Figure 12:
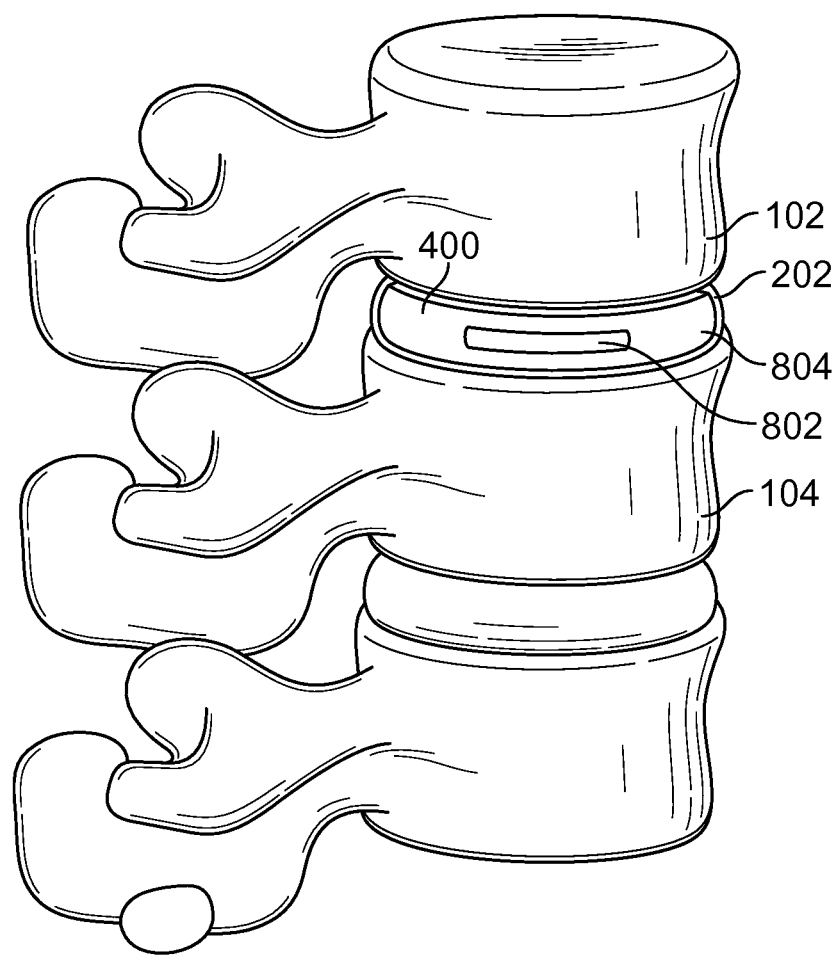
FIG. 12 is a cross-sectional view of an implant device deployed between vertebrae.

As the above demonstrates, chambers 802 and 804 may be simultaneously inflated, each with different materials. As illustrated in FIG. 12, this dual-chamber arrangement allows implant device 400 to fully support two adjacent vertebrae 102 and 104 while preserving a desirable degree of joint flexibility and shock protection. For instance, in some implementations outer chamber 804 may be inflated with an in situ curable silicone polymer while inner chamber 802 may be inflated with an inert gas. In such an arrangement, the silicone polymer hardens upon curing, allowing outer chamber 804 to act as firm, largely incompressible support structure between the two vertebrae. The gas-filled inner chamber 802 remains comparatively compressible, allowing implant device 400 to sustain sudden shocks and loads typical of active joint motion. Such an arrangement also preserves joint flexibility between two adjacent vertebrae, allowing for joint articulation.

A number of embodiments of the invention have been described. Nevertheless, it will be understood that various modifications may be made without departing from the spirit and scope of the invention. Accordingly, other embodiments are within the scope of the following claims.

Figure 13A:
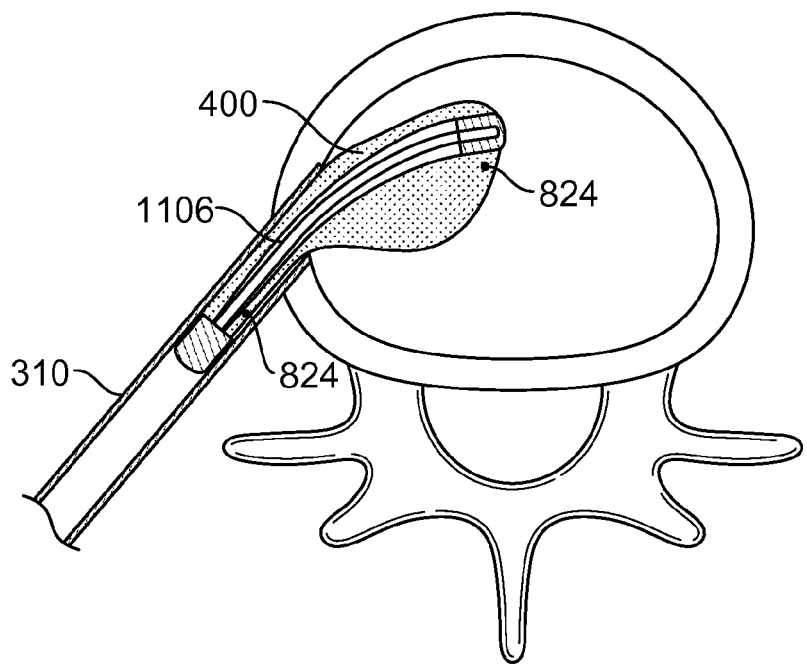
FIGS. 13A-C illustrate cross-sectional views of a non-symmetrically expanding embodiment of an implant device.
Figure 13B:
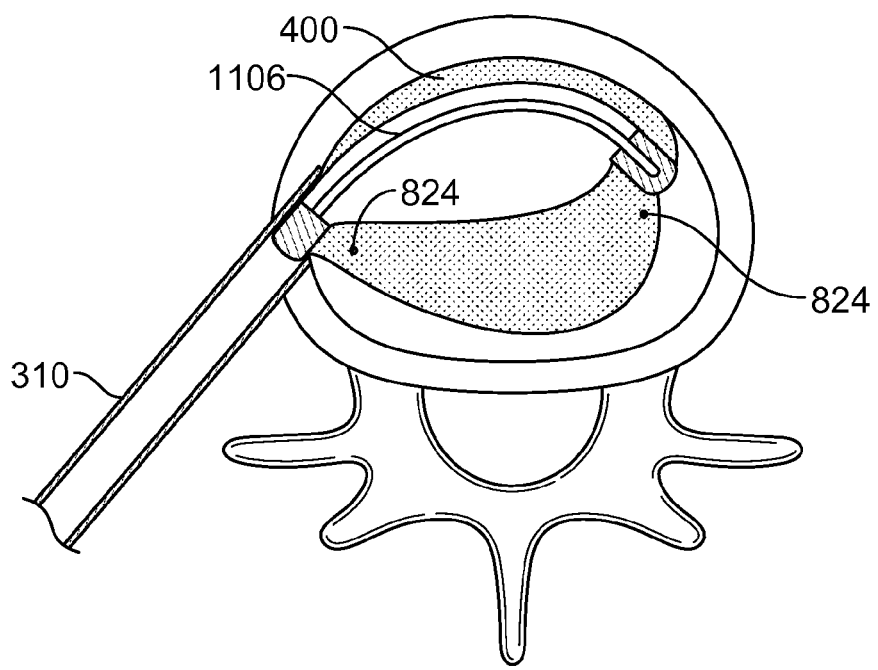
Figure 13C:
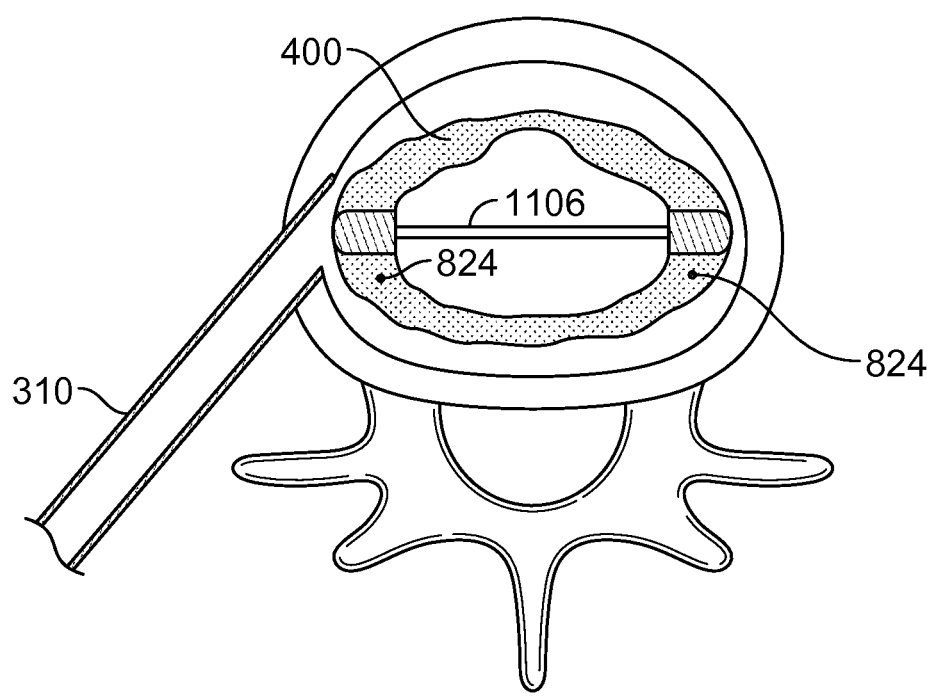

For example, while support wires 824 and 826 are illustrated above as largely symmetrical, with 824 and 826 arranged on either side of implant device 400, this need not be the case. For example, in some embodiments, one wire is removed such that implant device 400 directionally expands predominantly in only one direction when initially expelled from a cannula. This is illustrated in FIG. 13, where an embodiment of implant device 400 includes only one support wire 824. Referring to FIG. 13A, when implant device 400 is initially expelled from cannula 310, implant device 400 expands outward in a posterior direction, while it remains relatively unchanged in the anterior direction. As implant device 400 is inflated, expansion begins largely in the posterior portion expanded by wire 824, as illustrated in FIG. 13B. As inflation continues, the inflation substances are eventually distributed more evenly. When implant device 400 is fully inflated, as illustrated in FIG. 13C, implant device 400 is once again symmetrical. In some embodiments, fill tube 1106 is also made of a memory material alloy, such as nitinol, other shape memory alloy or a shape memory polymer, and is arranged to oppose the directional expansion of wire 824. In this manner, the expansion characteristics of implant device 400 may be varied to allow direction expansion when device 400 is initially placed, but to ensure symmetrical expansion when device 400 is fully inflated. Such embodiments are particularly advantageous when cannula 310 is inserted obliquely into an intervertebral disc, for example as illustrated in FIG. 13. In these embodiments, initial expansion of device 400 occurs largely in the posterior direction, reducing anteriorly-directed pressure against the annular fibrosis until device 400 approaches its fully inflated state. Further, such embodiments allow device 400 to fit more precisely against the annular fibrosis, as the anterior portion (without a support wire) is relatively flexible and can easily conform to the inner surface of the annular fibrosis.

Figure 14A:
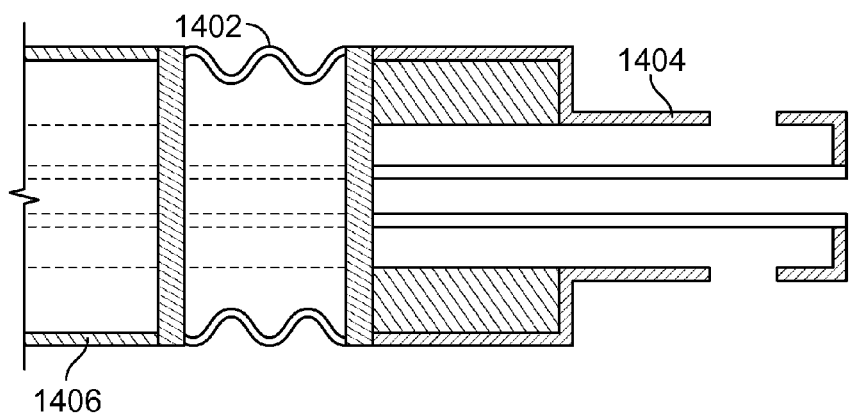
FIGS. 14A-B are cross-sectional views of alternative embodiments of a fill stylus.
Figure 14B:
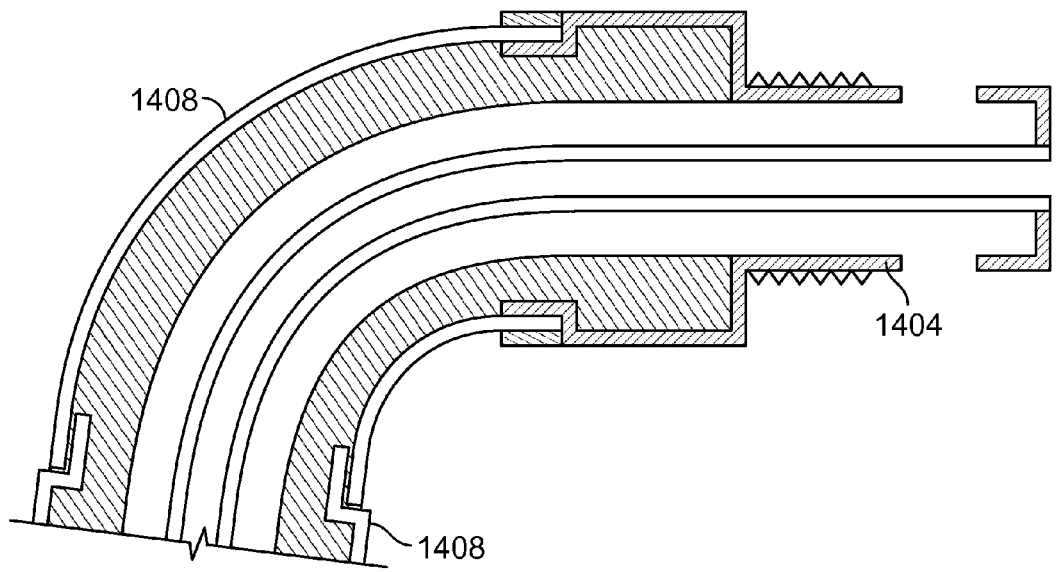

Fill stylus 1112 is described above as generally of a cylindrical shape. In some embodiments, the leading tip of fill stylus 1112 may have a bent or bendable leading tip, as illustrated in FIG. 13. As illustrated in FIG. 14A, fill stylus 1112 may have a flexible portion 1402, such that tip region 1404 may be articulated independently of body region 1406. In some embodiments, portion 1302 is a flexible material such as a rubber or silicone, such that tip 1404 moves when met with sufficient physical resistance. In some embodiments, the orientation of portion 1402 may be selectable by an operator, such that degree of bending may be selectively controlled during operation. As illustrated in FIG. 13B, tip region 1404 and body region 1406 may instead be connected by a bent region 1408. Bent region may be made of a memory material, such as nitinol, such that fill stylus 1112 may be deployed into the annular fibrosis through a cylindrical cannula, but while bend at region 1408 upon exiting the cannula, such that tip region 1404 is angled away from the axis of insertion.

In some embodiments, implant device 400 may be filled in a curable silicone, a curing compound, and an accelerating agent, such that the curing rate of the silicone may be modified as desired. Curing compounds and accelerating agents include platinum and platinum based compounds. Ultraviolet radiation, infrared radiation, and radio frequency excitation can also be used to cure the silicone. One or more of these materials may also include imaging contrast agents in order to provide imaging contrast for imaging modalities commonly employed in interventional radiology. Imaging modalities may include fluoroscopy, magnetic resonance imaging (MRI), computed tomography (CT), X-ray imaging, positron emission tomography (PET), or other medical imaging technique. Materials may include radiopaque materials, such that they are provide imaging contrast during x-ray or fluoroscopic procedures, paramagnetic or super paramagnetic materials, such that they provide imaging contrast during MRI, or other contrast agents commonly used with other imaging modalities.

In some embodiments, silicone instead be cured in other methods, such as though the application the UV energy or heat. In these embodiments, UV energy or heat may be applied through a tool adapted to fit into outer cannula 310 and operate within annular fibrosis 202. In some embodiments, fill stylus 1112 may include UV or heat energy-emitting elements, such that it may both fill and cure silicone.

Figure 15:
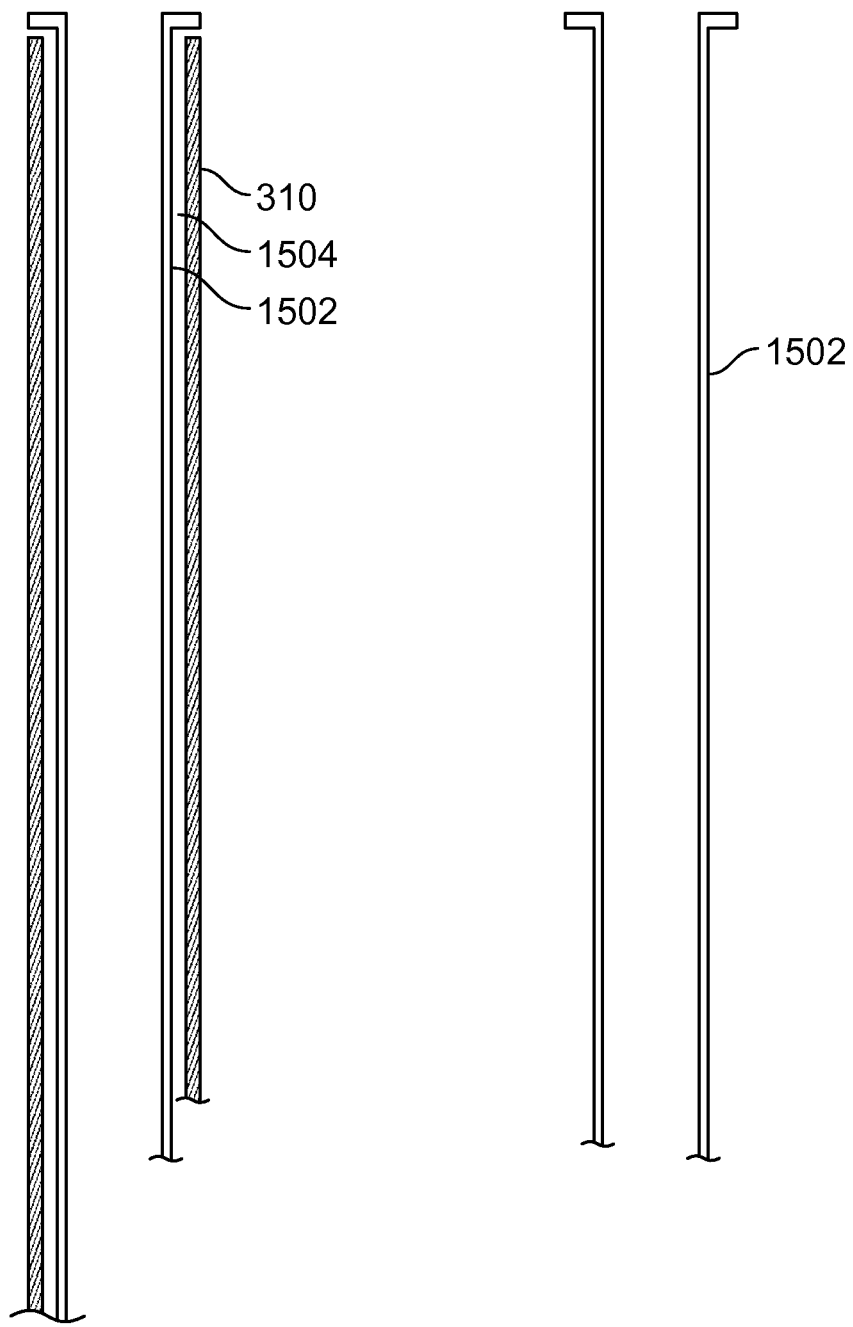
FIG. 15 is a cross-sectional view of a spacer element.
Figure 16:
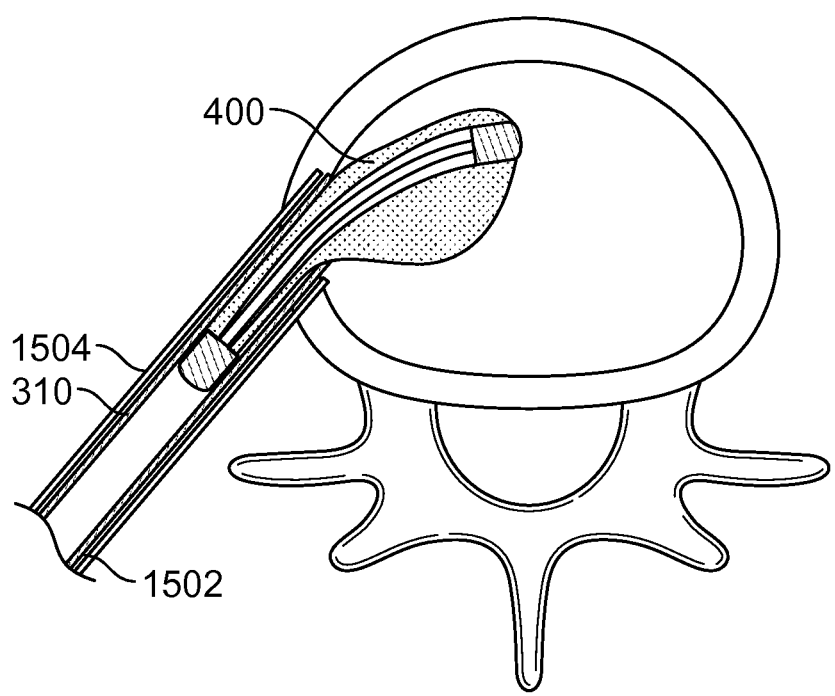
FIG. 16 illustrates an example usage of a spacer element during the insertion of an implant device.

In some embodiments, outer cannula 310 may additional include a vent channel 1504, such that air may be evacuated from within the surgical area during operation. This may be particular advantageous, for instance, during the insertion and inflation of implant device 400. As implant device 400 is inflated, displaced air is evacuated from the annular fibrosis, ensuring that no pockets of air become lodged within the annular fibrosis. This vent channel 1504 may be defined by a spacer element 1502, for example as illustrated in FIG. 15. Spacer element 1502 is tubular in shape and adapted to sildeably insert into outer cannula 310. Spacer element 1502 and outer cannula 310 are loosely connected to allow for air or other material to escape through vent channel 1504 when tools or materials are inserted into and advanced within spacer element 1502, for example as illustrated in FIG. 16. In some embodiments, a vent channel 1504 may be integrally defined into outer cannula 310 to similarly allow for the escape of air.

Alternate Embodiment of the Implant Device

In another example embodiment of an inter-vertebral implant device designed for percutaneous delivery and deployment, the implant device is likewise longitudinally collapsible for ease of insertion into a delivery cannula and is radially and longitudinally expandable within the disc space void following a percutaneous nuclectomy.

The implant device includes an outer textile band, for reinforcement of the annulus fibrosus and for stabilization of the vertebral segment. The band allows expansion of the nuclear implant to variable sizes in order to accommodate the size of the nuclear space following nuclectomy (nuclear removal), and to insure adequate contact with the inner wall of the annulus fibrosus. The band prevents migration of the implant device and provides support and stabilization function for the annulus fibrosus weakened by degeneration. The band also provides dynamic stability to the vertebral segment by limiting excessive mobility including abnormal degrees of forward and lateral bending, subluxation, and torsion. Thus, it restores support functions similar to the healthy annulus fibrosus. It also relieves the stress on the damaged annulus fibrosus by acting as an annular detente and redirecting the forces of outer expansion inwardly towards the inner gas chamber, thus promoting healing.

The annular reinforcement band is constructed of two hollow tubular braid sections that are overlapped and affixed to form a complete circle. Overlap of the lateral margins of these sections further reinforces the band. The textile reinforcement band is designed to be radially self-expanding and assume a C-shaped configuration by inserting a circular nitinol wire within its lumen to keep the braid flat and taut. The circular nitinol wire is restrained within the confines of the tubular braid and assumes an elongated oval shape, providing longitudinal expansion of the braid. The constrained nitinol wire also has memory to maintain the wire in a C configuration as viewed from the top, when expanded, providing radial expansion of the braid. The overlapped segments of tubular braid do not contain nitinol wire and are affixed to the outer margins of the dual-valve member and the tip-retainer member. Four fiber hinges are thus created at four corners of transition between the looping segments of nitinol wire constrained within the fiber braids and the overlapping lateral segments of the braids affixed to the outer margins of the dual-valve member on one side and the tip-retainer member on the other. Wire also has memory to maintain the wire in a C configuration as viewed from the top when expanded, providing radial expansion of the braid. Once the implant has been properly deployed within the disc space, it radially self-expands to come in intimate contact with the inner annulus. Inflation of the outer chamber with in-situ curable silicone, and the inner chamber with gas further applies outward pressure of the band and fixes it snugly along the inner annulus. Advantageously, it substantially conforms to the shape of the inner surface of the annulus.

Forming the reinforcement band out of a flattened tubular braid allows unhindered sliding motion between the two layers of the braid. This allows the outer layer of the braid, which is applied snugly against the inner annulus, to remain static while the inner layer retains its mobility. This promotes tissue ingrowth into the outer layer, promoting healing by allowing unhindered incorporation of the implant unto the annulus fibrosus. This also allows the nuclear implant to be removed at a later date if necessary, since the inner layer of the textile braid is unlikely to fuse to the annulus due to the sliding motion between the two layers.

The type of tubular braid used to form the reinforcement band may be varied. More specifically, the tubular braid of the present invention may be formed from a simple three yarn tubular braid or may be formed from a three dimensional braid. The flexible reinforcement band should accommodate a wide range of diameters reducing the need to precisely match the dimensions of the band to the outer circumference of the disc space.

A favorable combination of strength and flexibility can be achieved by selecting textile braids with particular properties, and by arranging these strands in particular ways, for example by altering the braiding angles of the strands and their axial spacing. Several textile braid constructions are contemplated that combine different kinds of strands, for example multifilament yarns, monofilaments with inter-braiding of a plurality of structural and textile strands that may be compliant or non-compliant. This achieves an integrated fattened tubular braid of structural braid of compliant and non-compliant structural strands and textile strands.

In one embodiment, the structural strands are polymeric and selectively shaped prior to the inter-braiding step. These can be formed into a variety of shapes that impart a predetermined configuration to the reinforcement band, most preferably helical. These are preferably wound as to sets of helices running in opposite directions.

In some embodiments, three-dimensional braiding is used instead of two-dimensional braiding, since three-dimensionally braided structures may have a more even distribution of forces among the strands.

Multi-filament yarns are also utilized, which have the advantage of a high degree of compliance and provide the needed flexibility to the band.

The tubular braids are designed to radially self-expand, with the help of the nitinol wire, with a force sufficient to allow proper deployment of the nuclear implant. However, the force of self-expansion provided by the nitinol wire is insufficient to anchor the implant against the inner annulus. Additional force is provided by the inflatable components and under image guidance and pressure monitoring during the procedure, whereby the band is forced radially outwardly into contact with the inner annulus. Measures are taken during manufacture to insure that the textile band, once the nuclear implant is deployed and inflated, will radially expand to the proper dimensions. This generally requires a careful matching of the reinforcement band dimensions to the nuclear cavity. Over-expansion of the implant places unnecessary stress on an already damaged annulus. Under expansion of the implant may result in inadequate contact of the reinforcement band with the inner annulus and migration of the implant may occur.

The degree to which the textile may stretch to substantially conform to the shape of the nuclear cavity is radially adjustable. Thus, the circumference of the nuclear space following nuclectomy need only to be approximated as described below.

In one embodiment, a thermoplastic yarn is used, and upon heat conditioning in the radially contracted state, the tubular braid becomes heat-set with elastomeric memory and intrinsic tendency to return to this state. This allows for easier folding of the implant to minimal profile for insertion into the delivery cannula during manufacturing. When released from the delivery cannula and deployed within the disc space, the braid has the flexibility to stretch or expand to the required dimensions, to a certain degree.

Since the self-expansion of the annular band is dependent on the shape memory of the incorporated nitinol wire, it is not necessary to include similar self-expansion memory properties in the braid. However, in some embodiments, such memory properties may also be included in the braid.

In another embodiment, to achieve a radially adjustable annular band, the braid may be formed on a specially designed mandrel having a circumference equal to the maximum expected circumference of the band. The width of the band can also be chosen accordingly.

In another embodiment, the tubular braid may be braided at a larger size and heat-set at a smaller size.

In order for the annular band to control the amount of expansion of the nuclear implant additional yarns that have limited compliance are braided into the structure. These additional yarns may course in a serpentine fashion along the radial and longitudinal axis of the braid in order to limit extreme degrees of radial and longitudinal mobility. This is designed to restore dynamic stability of the vertebral segment.

The implant device may also include an inflatable outer silicone membrane for containment of an outer chamber to be filled with in-situ curable rubber. The inflatable outer membrane has a generally discoid configuration upon inflation within the disc space. It has two mouth portions diametrically opposed from one another which are bonded to the outer faces of the dual-valve member on one side and the tip-retainer member on the other.

The implant device may also include an inflatable inner silicone membrane for containment of an inner chamber to be filled with gas. It has two mouth portions which are bonded or crimped into annular grooves formed around inward segments of the dual-valve and tip-retainer members.

The implant device may also include a dual-valve member that provides a reversible fluid communication with an inner and outer chamber. The dual-valve member can assume a closed configuration and an open configuration for both pathways.

The dual-valve member also provides surfaces for secure attachment of the textile band, and the outer and inner membranes, and a weight-bearing function after it is incorporated with the cured silicone in the outer chamber.

The dual-valve member includes a body being formed of a resilient material, such as silicone, having an elongate passageway extending there through, and two transverse pathways diametrically opposed from one another extend from the elongate passageway, substantially perpendicular to the longitudinal access, for delivery of curable silicone to the outer chamber of the nuclear implant.

In some embodiments, the body is shaped generally as a stepped cylinder that in cross-section has a straight-oval configuration. An outer surface of a body tapers inwardly to form an annular channel to secure the inner membrane to the dual-valve member proximally and to the tip-retainer distally. The body may be formed of any durable polymer that is pliable and resilient, such as silicone.

The outer chamber sealing member is shaped substantially as a smooth cylinder with the tubular member extending longitudinally in its center. It fits loosely within the elongate passageway formed in the body of the dual-valve member described above. It is formed of a thin-walled rigid material such as a polymer, and its surface is covered with a pliable and soft material that is capable of forming a seal when abutting the material of the body of the dual-valve member. In one embodiment, two protruding bosses are disposed along the outer margin of the outer chamber sealing member. These bosses are under tension and upon alignment of the aperture with the radial channels, the bosses snap outward into the radial channel, achieving a more secure occlusion on the fluid pathway.

The sealing member, with the tubular member affixed in its center, is translatable distally in the open configuration along the longitudinal axis wherein the sealing member uncovers the transverse pathways permitting fluid communication with the outer chamber, and occluding fluid flow in the closed configuration. Simultaneously, the tubular member is translatable distally, in unison, in the open configuration, exposing the lumen of the tubular member to the inner chamber, and is translatable proximally, in the closed configuration for establishing a gas-tight seal of the side opening of the tubular pathway.

The dual-valve member also includes a tubular member extending along a longitudinal axis of the dual-valve member and defining a second fluid pathway for delivery of gas to the inner chamber of the nuclear implant. The tubular member is open at its proximal end and closed at its distal end, and has a lateral opening at its middle section that is in reversible fluid communication with the inner chamber. It also provides mechanical support, stability, and proper alignment of the nuclear implant components especially during the process of nuclear implant deployment. The tubular member is made of shape memory material such as a metal (nitinol) or a polymer, to assume a C-shaped configuration when the implant is deployed in the disc space. The tip retainer member is guided posteriorly in order to orient the implant in the transverse plane of the disc. A flexible wire may extend through the gas passageway of the inflation stylus, and into the lumen of the tubular passageway of the nuclear implant, in order to provide further support and direction to the tip-retainer during delivery and deployment. The flexible wire is composed of shape-memory metal such as nitinol, and serves to guide the tip retainer into the transverse plane of the disc. The tubular member includes a connector terminal on the proximal end which is adapted to be coupled to the distal central aperture of the inflation stylus.

When the tubular member is translated proximally, a seal of the lateral opening of the tubular pathway is established, forming a gas tight sealing engagement. When the tubular member is translated distally, the lateral opening is in communication with the inner chamber and gas flow is established.

The tubular member is connected to the sealing member of the outer chamber and is translatable distally, in unison, in the open configuration, exposing the side opening of the tubular member for fluid communication with the inner chamber.

The sealing member of the inner chamber is cone shaped and is formed of a soft and pliable silicone.

The anterior wall of the dual-valve member is a relatively firm yet resilient plate that extends radially. It provides distal containment of the compression springs. It also provides a counter force for the crimping of the annular ring that secures the inner membrane to the body of the dual-valve member.

At least two compression springs are interposed between the sealing member proximally, and the anterior plate distally. They are rendered in the constrained state by being anteriorly displaced by the inflation stylus. Enough energy is stored in the springs such that upon removal of the inflation stylus, the sealing member and the tubular member are displaced proximally, sealing both chambers.

The dual-valve member also includes a tip-retainer member, identical in surface features to the dual-valve member that serves as the opposing site for attachment of the inner and outer membranes, and the textile band. However, the tip-retainer member does not provide a valve function. Instead, it harbors a longitudinal channel along its center for loose containment of the distal end of the tubular member.

The dual-valve member also includes a male inflation stylus for use with the female dual-valve member. This inflation stylus provides a fluid path for delivery of curable silicone to the outer chamber and a concentric central path for delivery of gas to the inner chamber. The inflation stylus includes an elongate nozzle that engages a receiving end of the nuclear implant so that the two components are removably engaged to one another, establishing alignment between the side opening of the inflation stylus with the transverse pathways of the body of the dual-valve member, thus establishing open fluid pathway communication with the outer chamber. The proximal aspect of the nozzle includes external threads that enable the nozzle to securely engage internal threads of the female body dual valve member by rotating the inflation stylus relative to the dual-valve member.

The steps of securing the male to female components are described below. The user begins by priming the inflation stylus with curable silicone. The user then positions the inflation stylus so that the distal face of the stylus abuts the proximal face of the sealing member at the inlet port. The user next applies digital pressure to push the sealing member distally until the threads of the inflation stylus engage the threads of the dual-valve member. At that point the user twists the inflation stylus while holding the delivery cannula containing the nuclear implant steady so that the engaged threads cause the inflation stylus to advance farther until the side openings of the inflation stylus are in perfect alignment with the transverse radial pathways, opening fluid communication between the inflation stylus and the outer chamber. Simultaneously, the tubular member advances the side opening of the tubular member, opening gas communication with the inner chamber.

In one embodiment, the inflation stylus stops advancing when the distal face of the nozzle contacts a proximally facing annular shoulder on the body of the dual-valve member.

When the nuclear implant is inflated to a desired size, the inflation stylus may be disconnected from the dual-valve member. To disengage the inflation stylus, the operator rotates the stylus in the opposite direction with respect to the dual-valve member. As the nozzle of the inflation stylus rotates, the engaged threads causes the nozzle to withdraw from the dual-valve member, and the sealing member and the tubular member are pushed back by the springs to the original positions, sealing both pathways. When the threads have completely disengaged, the operator pulls out the inflation stylus.

Alternate Embodiment of the Delivery Apparatus

In another example embodiment of the delivery apparatus, use of the delivery apparatus allows for placement of an access cannula into the intervertebral disc from a percutaneous poster-lateral approach, use of a mechanical nuclear evacuation device introduced via the access cannula into the disc space, and delivery of a mobile nuclear implant loaded in the delivery cannula introduced through the access cannula.

The apparatus includes an assembly shaped to accommodate the anatomical profile of the disc by having a straight-oval cross-section. The assembly includes a guide needle with a sharp pointed stylet, and an obturator that fits within the guide needle after the stylet is removed. The obturator has a blunt tip (to insure safety of cannula insertion into the disc space), an intermediate dilator body of uniform diameter, and a tail section of a smaller diameter. A shoulder is formed at a point of juncture between the intermediate end tail sections.

The apparatus includes a series of elongated tubular dilators adapted for telescopic mounting over the obturator.

The dilators are tubular in construction and straight-oval in cross-section, and are sized to fit snugly over each in telescopic manner. The dilators have tubular walls and are successively larger in diameter. Each dilator has a distal end, intermediate body, and a proximal end. A shoulder formed in the proximal end provides blocking means to restrict forward movement of the dilators over each other. The proximal aspect of each dilator has a flat surface with a central opening that accommodates the proximal thin section of the obturator.

An access cannula fits over the largest dilator and has a working channel. In some embodiments, this channel is approximately 5×8 mm. The access cannula lacks a fixed proximal blocking means. Instead, it has a removable cap, allowing for removal of the dilators while maintaining the access cannula in position.

A nuclear evacuation device and a nuclear implant are insertable into the working channel of the cannula. The removable cap is oval, and is generally cylindrical in shape. It has a flat top portion and a collar portion. The top portion has a centrally located opening that accommodates the tail section of the obturator. The collar portion fits loosely over the proximal end of the access cannula. The distal end of the access cannula is slanted, allowing for guidance such as a nuclear evacuation device or disc implant, into the disc space at a transverse orientation. Alternatively, the distal section of the access cannula may include a slanted redirecting element such as a curved or inclined surface. This surface may be concave and configured to conform to the convex surfaces of inserted delivery systems, nuclear evacuation device, or nuclear implant.

A perforated mallet fits over the smaller diameter tail section of the obturator and is used to introduce the dilators by tapping over the shoulders of the dilators and the cap component of the access cannula.

The proximal end of the access cannula is secured to the skin of the patient by an adjustable retaining ring, which is slid over the access cannula. A tightening screw is provided for secure yet adjustable fixation. The adjustable retaining ring secures the cannula tip firmly in place within the annulus fibrosus to prevent it from slipping. The ring encircles the cannula and is translatable along the length of the cannula. It is also provided with a flange for increased contact of the access cannula on the skin surface.

A thin-walled delivery cannula acts as a sleeve containing the folded nuclear implant in its proximal lumen. It is slidable into the access cannula in a loose fit, allowing for trapped air in the more distal aspect of the cannula to escape, as the loaded delivery cannula is advanced into the access cannula. The slanted tip of the delivery cannula is blunt and extends slightly beyond the sharp slanted tip of the access cannula.

In an example implementation, the delivery apparatus may be carried out under local anesthesia and conscious sedation, thus avoiding general anesthesia. First, the guide needle is inserted under imaging observation into the back of a prone patient in a postero-lateral approach. The needle is advanced in an oblique direction, (such as at an angle of 25 degrees with respect to the perpendicular plane), until the sharp tip of the stylet is inserted into the annulus fibrosus. The stylet is withdrawn and replaced by a blunt-tip obturator, which is advanced further into the disc space. The needle is then withdrawn, while the obturator is held in place by the operator. A series of dilators are sequentially introduced telescopically until their distal ends reach the inner margin of the annulus. The access cannula may then be inserted into the disc space. The cap is removed while the access cannula is held in place by the operator, and the obturator and dilators are then withdrawn together.

A nucleotome designed to fit loosely in the lumen of the access cannula is introduced through the access cannula and a complete nuclectomy is achieved. The nucleotome is then removed.

The user then primes the inflation stylus with curable silicone, attaches the stylus to the proximal end of the nuclear implant, which is loaded in the proximal aspect of the delivery cannula, and then advances the inflation stylus with the nuclear implant therein to the tip of the delivery cannula. After the nuclear implant is deployed, inflated, and pressurized, the inflation stylus is disconnected and the delivery cannula, together with the access cannula, is removed.

In an additional implantation of the present invention, a curable, flowable silicone is introduced into an implantable containment vessel in an uncured state. The silicone is then cured in vitro within the implantable containment vessel using a curing agent, UV radiation or RF excitation. For example, an implantable containment vessel, such as a balloon, bladder or the like, is implanted into a body cavity. Flowable curable silicon is injected into the implanted containment vessel using a syringe or specialized delivery stylus. In one implementation a curing agent, such as a platinum based compound is then injected into the silicone medium using either a syringe or an injection stylus. In another embodiment, a UV light source, such as a fiber optic cable is threaded through the syringe or provided in the specialized delivery stylus such that UV light is delivered to the injected silicone upon activation of the UV light source. In yet another implementation, flowable, curable silicone can be injected directly into to a body cavity, such as an evacuated intervertebral disk. Once delivered to the body cavity, the silicone can be cured as described above.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described components and systems can generally be integrated together in a single product or packaged into multiple products.

Thus, particular embodiments of the subject matter have been described. Other embodiments are within the scope of the following claims.

What is claimed is:

1. An implantable prosthetic device comprising:
an inner chamber;
an outer chamber fluidly isolated from the inner chamber; and
a sealing valve in fluid communication with the inner chamber and the outer chamber, the sealing valve comprising
a first sealing mechanism comprising a fill tube with a first aperture between an interior of the fill tube and an exterior of the fill tube, the fill tube being movable between an open position and a closed position,
a second sealing mechanism comprising a fill channel with a second aperture between an interior of the fill channel and an interior of the outer chamber, and a stopper element, the stopper element being slidable within the fill channel between an open position and a closed position, and
a biasing element for applying force to the stopper element to slide the stopper element into the closed position;
wherein when the sealing valve is in an open position, the first aperture of the first sealing mechanism is open to allow the inflow of a first material into the inner chamber and the stopper element is positioned so that the second aperture of the second sealing mechanism is open to allow fluid communication between the interior of the fill channel and the interior of the outer chamber to allow the inflow of a second material into the outer chamber;
wherein when the sealing valve is in a closed position, the first aperture of the first sealing mechanism is blocked to prevent outflow of the first material from within the inner chamber and the stopper element blocks the second aperture of the second sealing mechanism to prevent outflow of the second material from within the outer chamber;
wherein a force applied to the stopper element slides the stopper element into the open position to allow fluid communication between the interior of the fill channel and the interior of the outer chamber; and;
wherein the biasing element slides the stopper element toward the closed position to cause the sealing valve to enter the closed position when the force is released.

2. The device of claim 1, wherein the first material comprises an inert gas.

3. The device of claim 1, wherein the second material comprises a silicone polymer.

4. The device of claim 3, wherein the silicone polymer is curable.

5. The device of claim 1, wherein the second material comprises an imaging contrast agent.

6. The device of claim 1, further comprising an inflation device, the inflation device comprising:
a first channel; and
a second channel fluidly isolated from the first channel;
wherein the inflation device is adapted to apply the force to the stopper element, position the first channel in fluid communication with the inner chamber, position the second channel in fluid communication with the outer chamber, and simultaneously transfer the first material from the first channel to inner chamber and transfer the second material from the second channel to the outer chamber.

7. The device of claim 1, wherein the prosthetic device is collapsible.

8. The device of claim 1, wherein inflating the inner chamber or the outer chamber with a material causes the prosthetic device to expand.

9. The device of claim 1, further comprising a memory material, wherein the memory material expands the device to a pre-determined shape.

10. The device of claim 1, wherein the device is adapted to fit into a surgical cannula.

11. The device of claim 1, wherein the device is adapted for use as an intervertebral disc prosthesis.

12. The device of claim 11, wherein the device is configured to be implanted to fit adjacent a first vertebra against an upper surface and a second vertebra against a lower surface, such that the first vertebra is separated from the second vertebra.

13. A method of implanting a prosthetic device, comprising:
penetrating the annular fibrosus;
removing the nucleus pulposus;
implanting an inflatable device within the annular fibrosus, the inflatable device comprising:
an inner chamber;
an outer chamber fluidly isolated from the inner chamber; and
an inner chamber;
an outer chamber fluidly isolated from the inner chamber; and
a sealing valve in fluid communication with the inner chamber and the outer chamber, the sealing valve comprising
a first sealing mechanism comprising a fill tube with a first aperture between an interior of the fill tube and an exterior of the fill tube, the fill tube being movable between an open position and a closed position,
a second sealing mechanism comprising a fill channel with a second aperture between an interior of the fill channel and an interior of the outer chamber and a stopper element, the stopper element being slidable within the fill channel between an open position and a closed position, and
a biasing element for applying force to the stopper element to slide the stopper element into the closed position;
wherein when the sealing valve is in an open position, the first aperture of the first sealing mechanism is open to allow the inflow of a first material into the inner chamber and the stopper element is positioned so that the second aperture of the second sealing mechanism is open to allow fluid communication between the interior of the fill channel and the interior of the outer chamber to allow the inflow of a second material into the outer chamber;
wherein when the sealing valve is in a closed position, the first aperture of the first sealing mechanism is blocked to prevent outflow of the first material from within the inner chamber and the stopper element blocks the second aperture of the second sealing mechanism to prevent outflow of the second material from within the outer chamber;
wherein a force applied to the stopper element slides the stopper element into the open position to allow fluid communication between the interior of the fill channel and the interior of the outer chamber; and;

wherein the biasing element slides the stopper element toward the closed position to cause the sealing valve to enter the closed position when the force is released.

14. An implantable prosthetic device comprising:
an inner chamber;
an outer chamber fluidly isolated from the inner chamber;
a first sealing mechanism comprising a fill tube with a first aperture between an interior of the fill tube and an exterior of the fill tube, the fill tube being movable between an open position wherein the first aperture is open to allow fluid communication between the interior of the fill tube and the inner chamber and a closed position wherein the first aperture is blocked to prevent fluid communication between the interior of the fill tube and the inner chamber; and
a second sealing mechanism comprising:
 a fill channel with a second aperture between an interior of the fill channel and an interior of the outer chamber,
 a stopper element slidably mounted in the fill channel to slide between an open position wherein the second aperture is open to allow fluid communication between the interior of the fill channel and the outer chamber and a closed position wherein the second aperture is blocked by the stopper element to prevent fluid communication between the interior of the fill channel and the outer chamber, and
 a biasing element for applying force to the stopper element, wherein a force applied to the stopper element slides the stopper element into the open position and the biasing element urges the stopper element toward the closed position to cause the stopper element to enter the closed position when the force is released.

15. An implantable prosthetic device comprising:
an inner chamber;
an outer chamber fluidly isolated from the inner chamber;
a fill channel with an aperture for selectively allowing fluid communication between an interior of the outer chamber and the fill channel;
a stopper element slidably mounted in the fill channel for movement between a closed position and an open position, wherein in the closed position the stopper element blocks the fill channel aperture to prevent fluid communication between the interior of the outer chamber and the fill channel, and in the open position the stopper element is displaced from the fill channel aperture to allow fluid communication between the interior of the outer chamber and the fill channel;
a biasing element for urging the stopper element into the closed position; and
a fill tube with an aperture for selectively allowing fluid communication between an interior of the inner chamber and the fill tube, wherein the fill tube is slidably mounted between a closed position and an open position, wherein in the closed position the fill tube aperture is blocked to prevent fluid communication between the interior of the inner chamber and the fill tube, and in the open position the fill tube aperture is open to allow fluid communication between the interior of the inner chamber and the fill tube.

* * * * *